(12) United States Patent
Altenburger et al.

(10) Patent No.: US 8,697,731 B2
(45) Date of Patent: Apr. 15, 2014

(54) DERIVATIVES OF 2-PYRIDIN-2-YL-PYRAZOL-3(2H)-ONE, PREPARATION AND THERAPEUTIC USE THEREOF

(75) Inventors: Jean-Michel Altenburger, Paris (FR); Valérie Fossey, Paris (FR); Stéphane Illiano, Paris (FR); Géraldine Manette, Paris (FR)

(73) Assignee: Sanofi, Paris (FR)

( * ) Notice: Subject to any disclaimer, the term of this patent is extended or adjusted under 35 U.S.C. 154(b) by 106 days.

(21) Appl. No.: 13/172,321

(22) Filed: Jun. 29, 2011

(65) Prior Publication Data

US 2011/0301148 A1    Dec. 8, 2011

Related U.S. Application Data

(63) Continuation of application No. PCT/FR2009/052692, filed on Dec. 24, 2009.

(30) Foreign Application Priority Data

Dec. 29, 2008  (FR) ..................................... 08 07475
Aug. 28, 2009  (FR) ..................................... 09 04091

(51) Int. Cl.
*A61K 31/44* (2006.01)
*C07D 401/04* (2006.01)

(52) U.S. Cl.
USPC .................. 514/338; 546/278.4; 546/268.7

(58) Field of Classification Search
USPC ................................ 546/268.4, 268.7; 514/338
See application file for complete search history.

(56) References Cited

U.S. PATENT DOCUMENTS

| | | | |
|---|---|---|---|
| 5,175,176 | A | 12/1992 | Sasse et al. |
| 5,750,088 | A | 5/1998 | Sworin et al. |
| 2005/0187276 | A1 | 8/2005 | Park et al. |
| 2010/0035906 | A1 | 2/2010 | Flamme et al. |
| 2010/0305085 | A1 | 12/2010 | Thede et al. |

FOREIGN PATENT DOCUMENTS

| | | |
|---|---|---|
| EP | 0469357 | 2/1992 |
| WO | WO 2006/114213 | 11/2006 |
| WO | WO 2007/103905 | 9/2007 |
| WO | WO 2008/047198 | 4/2008 |
| WO | WO 2008/067871 | 6/2008 |
| WO | WO 2008/141731 | 11/2008 |

OTHER PUBLICATIONS

ChemSpider "structure 724154" (2012).*
Ban et al. "Hypoxia-indicible. . ." Exp. Opin.Ther. Patents 21(2) p. 131-146 (2011).*
Baroni et al. "New derivatives . . ." CA155:182079 (2011).*
Dorwald "Side reactions. . ." p. ix (2005).*
Jordan "Tamoxifen . . ." Nature Rev. v.2, Mar. p. 205-213 (2003).*
Improper Markush guideline p. 1-2 (2011).*
Kunz et al. "Preparation of n- . . ." CA131:359785 (1999).*
U.S. Appl. No. 13/172,305, filed Jun. 29, 2011, Altenburger, et al.
Eglen, R.M., et al., Enzyme Fragment Complementation: A Flexible High Throughput Screening Assay Technology, Assay and Drug Development Technologies, vol. 1, No. 1, (2002), pp. 97-104.
Bonjoch, J., et al., Synthesis of 2,5-piperidinediones. Regioselectivity in the Dieckmann Cyclization, Tetrahedron, vol. 40, No. 13, pp. 2505-2511, (1984).
Buechi, J., et al., Synthesis and Phamacological Properties of Certain Pyridylpyrazol-5-Ones, Helvetica Chimica Acta, (1966), vol. 49, No. 1, pp. 272-280.
Conroy, et al., Using the Electrostatic Field Effect to Design a New Class of Inhibitors for Cysteine Proteases, J. Am. Chem. Soc., (1997), vol. 119, pp. 4285-4291.
Eglen, R. M., et al., B Galactosidase Enzyme Fragment Complementation as A Novel Technology for High Throughput Screening , Combinatorial Chemistry & High Throughput Screen, vol. 6, pp. 381-387, (2003).
International Search Report for WO2010/076525 dated Jul. 8, 2010.

* cited by examiner

*Primary Examiner* — Celia Chang
(74) *Attorney, Agent, or Firm* — Scully, Scott, Murphy & Presser, P.C.

(57) ABSTRACT

The invention relates to compounds corresponding to formula (I), in the form of the base or of an acid-addition salt:

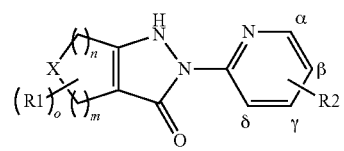

in which n is equal to 0, 1, 2, 3 or 4; m is equal to 0, 1 or 2; o is equal to 0 or 1; X represents a group —$CH_2$, —CH(R')—, —NH(R')— or a heteroatom chosen from O and S, it being understood that R' represents a group —(C1-C5)alkyl, —(C1-C5)alkoxy, —$CH_2$-aryl, —C(O)R5 or —COOR5; R1, R2, R5 are as defined in the specification.

13 Claims, No Drawings

DERIVATIVES OF 2-PYRIDIN-2-YL-PYRAZOL-3(2H)-ONE, PREPARATION AND THERAPEUTIC USE THEREOF

This application is a Continuation of International Application No. PCT/FR2009/052692, filed Dec. 24, 2009, which is incorporated herein by reference in its entirety.

The present invention relates to novel substituted dihydropyrazolone derivatives, to their preparation and to their therapeutic use as activators of the transcription factor HIF.

Hypoxia-inducible factor (HIF) (HIF1-alpha) is a transcription factor that is constitutively expressed in all tissues. This protein was discovered in 1994 by Gregg Semenza during studies on the regulatory sequences of the EPO gene. He identified a sequence located in the non-coding 3' position in the EPO promoter, which bears the name "hypoxia response element" (HRE) and which is a site of binding of the protein HIF1-alpha allowing transcriptional activation of EPO. Thereafter, the HRE sequence was also located on more than 70 other genes, such as VEGF (vascular endothelial growth factor) or Glut1 (glucose transporter 1). The transcriptional complex HIF-1 is at the minimum a heterodimer formed from the protein HIF1-alpha or HIF2-alpha and another transcription factor ARNT (formerly known as HIF1-alpha). ARNT is constitutively and stably expressed in cells and the main part of the transcription complex regulation is associated with the amount of HIF1-alpha present in the cells, which is thus the limiting factor.

Under normal oxygen conditions, the protein HIF1-alpha is rapidly degraded (half-life of 5 minutes). This degradation follows the hydroxylation of HIF1-alpha or HIF2-alpha, respectively, on prolines 402 and 563 and prolines 405 and 531 for the human forms with HIF prolyl hydroxylase (HIF-PHDs or EGLNs). This hydroxylation allows binding of the Von Hippell Lindau protein (pVHL) associated with a ubiquitin ligase, which results in the degradation of HIF1-alpha or HIF2-alpha by the ubiquitin proteasome system. When the cell or tissue are subjected to high hypoxia/ischaemia, HIF1-alpha or HIF2-alpha is no longer degraded by the ubiquitin-proteasome system and can then combine with the other transcription factors of the HIF complex to transfer into the nucleus and activate their target genes.

Although high hypoxia is the main cause of activation of the proteins HIF1-alpha and HIF2-alpha, other inducers, such as insulin and growth factors, may also play a role in their stabilization, especially via phosphorylation on their serines 641 and 643.

Phenotypic screening directed towards measuring the stabilization of the protein HIF1-alpha and/or HIF2-alpha was thus established to identify the compounds of the present invention.

The compounds according to the present invention correspond to formula (I) below:

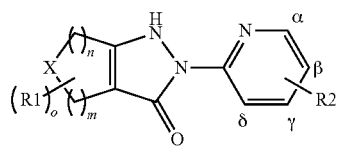

in which
n is equal to 0, 1, 2, 3 or 4;
m is equal to 0, 1 or 2;
o is equal to 0 or 1;
X represents a group —CH$_2$—, —CH(R')—, —N(R')— or a heteroatom chosen from an oxygen atom and a sulfur atom, it being understood that R' represents a group —(C1-C5)alkyl, —(C1-C5)alkoxy, —CH$_2$-aryl, —C(O)R5 or —COOR5 with R5 as defined below;
R1 represents an oxo group, a group —COOR5, a group —W—OH or a group —W—NR5R6, with W, R5 and R6 as defined below; and
R2 represents a hydrogen atom or a group chosen from (i) groups —(C1-C5)alkyl, (ii) groups —(C1-C5)alkoxy, (iii) groups —COOR5, (iv) groups —NR5R6, (v) groups —C(O)—NR5R6, (vi) groups —SO$_2$—NR3R4, (vii) heteroaryl groups optionally substituted with a group —(C1-C5)alkyl, (viii) groups —W-aryl, (ix) groups —W-heteroaryl, (x) groups —O—W-aryl, (xi) groups —O—W-heteroaryl and (xii) groups —O—W—NR5R6, with W, R3, R4, R5 and R6 as defined below; it being understood that:
R3 and R4,
(i) which may be identical or different, represent, independently of each other, a hydrogen atom, a group —(C1-C5)alkyl, a group —(C3-C6)cycloalkyl, an aryl group, a heteroaryl group, a group —CH$_2$-heteroaryl, a group —(C1-C5)alkyl-NR5R6, a group —W—OH or a group —W—NR5R6; or
(ii) form, together with the nitrogen atom that bears them, a heterocycloalkyl group optionally substituted with one or more groups chosen from groups —(C1-C5)alkyl and groups —CH$_2$-aryl;
W is a group —(C1-C5)alkylene, optionally substituted with one or more hydroxyl groups; and
R5 and R6, which may be identical or different, represent, independently of each other, a hydrogen atom or a group chosen from groups —(C1-C5)alkyl and groups —(C3-C6)cycloalkyl.

The compounds of formula (I) may exist in the form of bases or salts, the compounds of formula (I) having been, in this case, salified with acids or bases, especially pharmaceutically acceptable acids or bases. They are then referred to as addition salts, in particular salts of addition to an acid or a base, which form part of the invention. The salts are advantageously prepared with pharmaceutically acceptable acids, but the salts of other acids that are useful, for example, for purifying or isolating the compounds of formula (I) also form part of the invention. Mention may be made of hydrochloride salts, trifluoroacetic acid salts and sodium salts.

The compounds of formula (I) may also exist in the form of solvates, i.e. in the form of associations or combinations with one or more solvent molecules. Such solvents also form part of the invention.

When o is equal to 0, then the ring comprises only hydrogen atoms.

The various tautomeric forms of the compounds of formula (I) also form part of the invention:

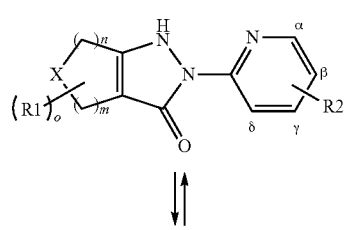

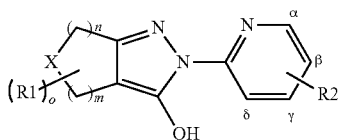

Furthermore, a subject of the invention is also a uniform test for the direct measurement by beta-galactosidase complementation of the amount of HIF1-alpha protein in the nucleus of cells, preferably HEK cells, after treating the said cells with one or more test compounds, which consists in:
(a) inoculating, preferably in 384-well plates, the said cells in a suitable culture medium, preferably 1% foetal calf serum (abbreviated as FCS);
(b) adding the test compound(s) at a suitable concentration in a suitable solvent to the cells previously inoculated in the said culture medium; preferably the test compounds are diluted in 0.1% FCS;
(c) incubating the said cells thus prepared in an indicator at about 37° C., advantageously for about 6 hours;
(d) lysing the cells with a lysis buffer containing a chemiluminescent substrate for beta-galactosidase;
(e) incubating in the absence of light, before reading and measuring the luminescence, which is a function of the beta-galactosidase activity.

The compounds according to the invention underwent a screening test according to the test as defined above.

In the context of the present invention, and unless otherwise mentioned in the text, the following definitions apply:
a halogen atom: a fluorine, chlorine, bromine or iodine atom;
an alkyl group: a linear or branched, saturated aliphatic group, which may contain 1, 2, 3, 4 or 5 carbon atoms (abbreviated as —(C1-C5)alkyl). Examples that may be mentioned include, as (i) group —C1alkyl, the methyl group, as (ii) group —C2alkyl, the ethyl group, as (iii) group —C3alkyl, the propyl or isopropyl group, as (iv) group —C4alkyl, the butyl, isobutyl or tert-butyl group, as (v) group —C5alkyl the pentyl or isopentyl group;
an alkylene croup: a linear or branched, saturated divalent alkyl group as defined previously, which may contain 1, 2, 3, 4 or 5 carbon atoms (abbreviated as —(C1-C5) alkylene-). Examples that may be mentioned include methylene (or —CH$_2$—), ethylene (or —CH$_2$—CH$_2$—) or propylene (—CH$_2$—CH$_2$—CH$_2$—) groups;
a cycloalkyl croup: a cyclic alkyl group which may contain 3, 4, 5 or 6 carbon atoms, also abbreviated as —(C3-C6) cycloalkyl. Examples that may be mentioned include cyclopropyl, cyclobutyl, cyclopentyl and cyclohexyl groups;
an alkoxy croup: a radical —O-alkyl in which the alkyl group is as defined previously. Examples that may be mentioned include the groups —O—(C1-C5)alkyl or —(C1-C5)alkoxy, and in particular, as (i) group —O—C1alkyl, the group —Omethyl, as (ii) group —O—C2alkyl, the group —Oethyl, as (iii) group —O—C3alkyl, the group —Opropyl or —Oisopropyl, as (iv) group —O—C4alkyl, the group —Obutyl, —Oisobutyl or —Otert-butyl, as (v) group —O—C5alkyl the group —Opentyl or —Oisopentyl;
an alkoxy-alkyl group: a radical -alkylene-O-alkyl, in which the alkyl and alkylene groups, comprising the same number of carbon atoms or not comprising the same number of carbon atoms, are as defined previously. Examples that may be mentioned include groups —(C1-C5)alkylene-O—(C1-C5)alkyl, with —(C1-C5) alkylene- and —(C1-C5)alkyl as defined above;
a haloalkyl group: an alkyl group as defined above, substituted with 1, 2, 3, 4 or 5 halogen atoms, as defined previously. Examples that will be mentioned include groups -halo(C1-C5)alkyl, with (C1-C5)alkyl as defined above, and in particular the trifluoromethyl group (abbreviated as —CF$_3$);
an aryl group: a cyclic aromatic group containing 5 or 6 carbon atoms. An example of aryl groups that may be mentioned is the phenyl group;
a heteroaryl group: a cyclic aromatic group containing 2, 3, 4 or 5 carbon atoms and comprising 1 to 3 heteroatoms, which may be chosen from a nitrogen atom, an oxygen atom and a sulfur atom, independently of each other, so as to be identical or different, when there are 2 of them, or independently of each other, so as to be identical or different, when there are 3 of them. Mention may be made of pyridyl, pyrrol and furyl groups;
a heterocycloalkyl: an optionally bridged cyclic alkyl group, containing 5, 6 or 7 carbon atoms and comprising 1, 2 or 3 heteroatoms which may be chosen, independently of each other, so as to be identical or different, when there are 2 of them, or independently of each other, so as to be identical or different, when there are 3 of them, from a nitrogen atom, an oxygen atom and a sulfur atom. Mention may be made especially of piperidyl, piperazinyl, pyrrolidinyl, hexamethyleneimino, morpholinyl and 1,1-dioxidotetrahydrothienyl groups;
the letters α, β, γ and δ around the pyridine of the compounds of formula (I) serve to identify the positions of the various carbon atoms.

Among the compounds described in the present invention, mention may be made of a first group of compounds corresponding to formula (I) in which:
n is equal to 0, 1, 2, 3 or 4,
and/or
m is equal to 0, 1 or 2,
and/or
o is equal to 0 or 1,
and/or
X represents a group —CH$_2$—, —CH(R')—, —N(R')— or a heteroatom chosen from an oxygen atom and a sulfur atom,
and/or
R' represents a group —(C1-C5)alkyl, a group —(C1-C5) alkoxy, a group —CH$_2$-aryl, a group —C(O)R5 or a group —COOR5;
and/or
R1 represents an oxo group, a group —COOR5, a group —W—OH or a group —W—NR5R6;
and/or
R2 represents a hydrogen atom, a group —(C1-C5)alkyl, a group —(C1-C5)alkoxy, a group —COOR5, a group —NR5R6, a group —C(O)—NR5R6 or a group —SO$_2$— NR3R4;
and/or
R3 and R4
(i) represent, independently of each other, a hydrogen atom, a group —(C1-C5)alkyl, a group —(C3-C6)cycloalkyl, an aryl group, a heteroaryl group, a group —CH$_2$-heteroaryl or a group —(C1-C5)alkyl-NR5R6; or
(ii) form, together with the nitrogen atom that bears them, a heterocycloalkyl group optionally substituted with a group —(C1-C5)alkyl or with an aryl group, and/or W represents a group —(C1-C5)alkylene, optionally substituted with one or more hydroxyl groups;

and/or

R5 and R6 represent, independently of each other, a hydrogen atom or a group —(C1-C5)alkyl.

A first subgroup of compounds of the invention is formed by the compounds of formula (I) in which n is equal to 0, 1, 2, 3 or 4.

A second subgroup of compounds of the invention is formed by the compounds of formula (I) in which m is equal to 0, 1 or 2.

A third subgroup of compounds of the invention is formed by the compounds of formula (I) in which o is equal to 0.

A fourth subgroup of compounds of the invention is formed by the compounds of formula (I) in which R1 represents an oxo group, a group —CH$_2$-aryl, a group —C(O)R5- or a group —COOR5, the said group R1 possibly being linked to a carbon atom or a heteroatom. Advantageously, the aryl group represents a phenyl group.

A fifth subgroup of compounds of the invention is formed by the compounds of formula (I) in which R2 represents (i) a hydrogen atom, (ii) a group —(C1-C5)alkyl, (iii) a group —(C1-C5)alkoxy, (iv) a group —COOR5, (v) a group —NR5R6, (vi) a group —C(O)—NR5R6, (vii) a heteroaryl substituted with a group —(C1-C5) alkyl, (viii) a group —O—W-aryl or (ix) a group —O—W-heteroaryl.

A sixth subgroup of compounds of the invention is formed by the compounds of formula (I) in which R2 represents a group —SO$_2$—NR3R4.

A seventh subgroup of compounds of the invention is formed by the compounds of formula (I) in which R2 is a substituent on the atom in the beta position of pyridine.

An eighth subgroup of compounds of the invention is formed by the compounds of formula (I) in which R2 is a substituent on the atom in the gamma position of pyridine.

A ninth subgroup of compounds of the invention is formed by the compounds of formula (I) in which R3 and R4 represent, independently of each other, a hydrogen atom, a group —(C1-C5)alkyl, a group —(C3-C6)cycloalkyl, an aryl group, a heteroaryl group, a group —CH$_2$-heteroaryl or a group —(C1-C5)alkyl-NR5R6. Advantageously, the aryl group represents a phenyl group and the heteroaryl group represents a pyridyl group or a furyl group.

A tenth subgroup of compounds of the invention is formed by the compounds of formula (I) in which R3 and R4 form, together with the nitrogen atom that bears them, a heterocycloalkyl group optionally substituted with one or more group(s) —(C1-C5)alkyl and/or aryl. Advantageously, the heterocycloalkyl group represents a piperidyl group, a pyrrolidinyl group or a hexamethyleneimino group and the aryl group represents a phenyl group.

An eleventh subgroup of compounds of the invention is formed by the compounds of formula (I) in which R5 represents a group —(C1-C5)alkyl or a group —(C1-C5)cycloalkyl.

A twelfth subgroup of compounds of the invention is formed by the compounds of formula (I) in which R6 represents a hydrogen atom or a group (C1-C5)alkyl.

The subgroups defined above, taken separately or in combination, also form part of the invention.

Among the compounds described in the present invention, mention may also be made of a subgroup of compounds corresponding to formula (I) in which:

n is equal to 1, 2, 3 or 4;

m is equal to 0, 1 or 2;

o is equal to 0 or 1;

X represents a —CH$_2$— group, a group —CH(R')—, a group —N(R')— or a heteroatom chosen from an oxygen atom and a sulfur atom;

R' represents a group —(C1-C5)alkyl, a group —(C1-C5)alkoxy, a group —CH$_2$-aryl, a group —C(O)R5 or a group —COOR5;

R1 represents an oxo group, a group COOR5, a group —W—OH or a group —W—NR5R6;

R2 represents a group —SO$_2$—NR3R4;

R3 and R4 represent, independently of each other, a hydrogen atom, a group —(C1-C5)alkyl, a group —(C3-C6)cycloalkyl, an aryl group, a heteroaryl group or a group —CH$_2$-heteroaryl, or R3 and R4 form, together with the nitrogen atom that bears them, a heterocycloalkyl group; and R5 and R6 represent a group —(C1-C5)alkyl.

Among the compounds described in the present invention, mention may be made, finally, of a subgroup of compounds corresponding to formula (I) in which:

n is equal to 1, 2, 3 or 4;

m is equal to 0, 1 or 2;

o is equal to 0 or 1;

X represents a group —CH$_2$—, a group —CH(R')—, a group —N(R')— or a heteroatom chosen from an oxygen atom and a sulfur atom;

R' represents a group —(C1-C5)alkyl, a group —(C1-C5)alkoxy, a group —CH$_2$-aryl, a group —C(O)R5 or a group —COOR5;

R1 represents an oxo group;

R2 represents a hydrogen atom, a group —(C1-C5)alkyl, a group —(C1-C5)alkoxy, a group —COOR5, a group —NR5R6 or —C(O)—NR5R6; and R5 and R6 represent, independently of each other, a hydrogen atom, a group —(C1-C5)alkyl or a group —(C1-C5)cycloalkyl.

Among the compounds of formula (I) that are subjects of the invention, mention may be made especially of the following compounds:

2-[5-(piperidin-1-ylsulfonyl)pyridin-2-yl]-1,2,4,5,6,7-hexahydro-3H-indazol-3-one;

6-methyl-2-[5-(piperidin-1-ylsulfonyl)pyridin-2-yl]-1,2,4,5,6,7-hexahydro-3H-indazol-3-one;

2-[5-(piperidin-1-ylsulfonyl)pyridin-2-yl]-1,4,5,6,7,8-hexahydrocyclohepta[c]pyrazol-3(2H)-one;

N-ethyl-6-(3-oxo-1,3,4,5,6,7-hexahydro-2H-indazol-2-yl)-N-phenylpyridine-3-sulfonamide;

6-(5-benzyl-3-oxo-1,3,4,5,6,7-hexahydro-2H-pyrazolo[4,3-c]pyridin-2-yl)-N-ethyl-N-phenylpyridine-3-sulfonamide;

(±)-2-(5-{[(3R,5S)-3,5-dimethylpiperidin-1-yl]sulfonyl}pyridin-2-yl)-1,2,4,5,6,7-hexahydro-3H-indazol-3-one;

2-(4-methoxypyridin-2-yl)-1,2,4,6-tetrahydro-3H-thieno[3,4-c]pyrazol-3-one;

2-(pyridin-2-yl)-1,4,5,6-tetrahydrocyclopenta[c]pyrazol-3(2H)-one;

(±)-5-benzyl-2-(5-{[(3R,5S)-3,5-dimethylpiperidin-1-yl]sulfonyl}pyridin-2-yl)-1,2,4,5,6,7-hexahydro-3H-pyrazolo[4,3-c]pyridin-3-one;

(±)-2-(5-{[(3R,5S)-3,5-dimethylpiperidin-1-yl]sulfonyl}pyridin-2-yl)-6-methyl-1,2,4,5,6,7-hexahydro-3H-indazol-3-one;

6-(5-benzyl-3-oxo-1,3,4,5,6,7-hexahydro-2H-pyrazolo[4,3-c]pyridin-2-yl)-N,N-diethylpyridine-3-sulfonamide;

N-ethyl-6-(3-oxo-1,3,4,5,6,7,8,9-octahydro-2H-cycloocta[c]pyrazol-2-yl)-N-phenylpyridine-3-sulfonamide;

N-ethyl-6-(3-oxo-4,6-dihydro-1H-thieno[3,4-c]pyrazol-2 (3H)-yl)-N-phenylpyridine-3-sulfonamide;
6-(5-benzyl-3-oxo-1,3,4,5,6,7-hexahydro-2H-pyrazolo[4,3-c]pyridin-2-yl)-N,N-di(propan-2-yl)pyridine-3-sulfonamide;
6-methoxy-2-(pyridin-2-yl)-1,4,5,6-tetrahydrocyclopenta[c]pyrazol-3(2H)-one;
2-(pyridin-2-yl)-1,4,6,7-tetrahydrothiopyrano[4,3-c]pyrazol-3(2H)-one;
N-ethyl-6-(3-oxo-1,4,6,7-tetrahydrothiopyrano[4,3-c]pyrazol-2(3H)-yl)-N-phenylpyridine-3-sulfonamide;
N-ethyl-6-(3-oxo-3,5,6,7-tetrahydrothiopyrano[3,2-c]pyrazol-2(1H)-yl)-N-phenylpyridine-3-sulfonamide;
N,N-diethyl-6-(3-oxo-4,6-dihydro-1H-thieno[3,4-c]pyrazol-2(3H)-yl)pyridine-3-sulfonamide;
N,N-dimethyl-6-(3-oxo-4,6-dihydro-1H-thieno[3,4-c]pyrazol-2(3H)-yl)pyridine-3-sulfonamide;
2-[5-(pyrrolidin-1-ylsulfonyl)pyridin-2-yl]-1,2,4,6-tetrahydro-3H-thieno[3,4-c]pyrazol-3-one;
N-cyclopropyl-6-(3-oxo-4,6-dihydro-1H-thieno[3,4-c]pyrazol-2(3H)-yl)pyridine-3-sulfonamide;
6-(3-oxo-4,6-dihydro-1H-thieno[3,4-c]pyrazol-2(3H)-yl)-N-(propan-2-yl)pyridine-3-sulfonamide;
N-tert-butyl-6-(3-oxo-4,6-dihydro-1H-thieno[3,4-c]pyrazol-2(3H)-yl)pyridine-3-sulfonamide;
N-(furan-2-ylmethyl)-6-(3-oxo-4,6-dihydro-1H-thieno[3,4-c]pyrazol-2(3H)-yl)pyridine-3-sulfonamide;
N-cyclopentyl-6-(3-oxo-4,6-dihydro-1H-thieno[3,4-c]pyrazol-2(3H)-yl)pyridine-3-sulfonamide;
N-methyl-6-(3-oxo-4,6-dihydro-1H-thieno[3,4-c]pyrazol-2(3H)-yl)-N-(pyridin-2-yl)pyridine-3-sulfonamide;
2-(pyridin-2-yl)-1,2,4,6-tetrahydro-3H-thieno[3,4-c]pyrazol-3-one;
2-[4-(dimethylamino)pyridin-2-yl]-1,2,4,6-tetrahydro-3H-thieno[3,4-c]pyrazol-3-one;
2-{5-[(4-benzylpiperidin-1-yl)sulfonyl]pyridin-2-yl}-1,2,4,6-tetrahydro-3H-thieno[3,4-c]pyrazol-3-one;
6-(3-oxo-4,6-dihydro-1H-thieno[3,4-c]pyrazol-2(3H)-yl)-N-(pyridin-2-yl)pyridine-3-sulfonamide;
N-ethyl-6-(3-oxo-1,4,6,7-tetrahydropyrano[4,3-c]pyrazol-2(3H)-yl)-N-phenylpyridine-3-sulfonamide;
sodium 2-(4-ethylpyridin-2-yl)-2,6-dihydro-4H-thieno[3,4-c]pyrazol-3-olate;
2-[5-(azepan-1-ylsulfonyl)pyridin-2-yl]-1,2,4,6-tetrahydro-3H-thieno[3,4-c]pyrazol-3-one;
sodium 4-benzyl-2-{5-[ethyl(phenyl)sulfamoyl]pyridin-2-yl}-5-oxo-4,5,6,7-tetrahydro-2H-pyrazolo[4,3-b]pyridin-3-olate;
N-methyl-6-(3-oxo-4,6-dihydro-1H-thieno[3,4-c]pyrazol-2(3H)-yl)-N-(pyridin-2-ylmethyl)pyridine-3-sulfonamide;
tert-butyl 2-{5-[ethyl(phenyl)sulfamoyl]pyridin-2-yl}-3-oxo-1,2,3,4,6,7-hexahydro-5H-pyrazolo[4,3-c]pyridine-5-carboxylate;
6-(5-acetyl-3-oxo-1,3,4,5,6,7-hexahydro-2H-pyrazolo[4,3-c]pyridin-2-yl)-N-ethyl-N-phenylpyridine-3-sulfonamide;
tert-butyl 6-(3-oxo-4,6-dihydro-1H-thieno[3,4-c]pyrazol-2(3H)-yl)pyridine-3-carboxylate;
sodium 2-(4-methylpyridin-2-yl)-2,6-dihydro-4H-thieno[3,4-c]pyrazol-3-olate;
sodium 2-{5-[tert-butyl(methyl)sulfamoyl]pyridin-2-yl}-2,6-dihydro-4H-thieno[3,4-c]pyrazol-3-olate;
sodium 2-{5-[tert-butyl(ethyl)sulfamoyl]pyridin-2-yl}-2,6-dihydro-4H-thieno[3,4-c]pyrazol-3-olate;
sodium 2-(5-methylpyridin-2-yl)-2,6-dihydro-4H-thieno[3,4-c]pyrazol-3-olate;
sodium 2-[5-(tert-butylcarbamoyl)pyridin-2-yl]-2,6-dihydro-4H-thieno[3,4-c]pyrazol-3-olate;
sodium 2-(5-methoxypyridin-2-yl)-2,6-dihydro-4H-thieno[3,4-c]pyrazol-3-olate;
N-methyl-6-(3-oxo-4,6-dihydro-1H-thieno[3,4-c]pyrazol-2(3H)-yl)-N-(pyridin-4-yl)pyridine-3-sulfonamide;
sodium 2-{5-[cyclopentyl(ethyl)sulfamoyl]pyridin-2-yl}-2,6-dihydro-4H-thieno[3,4-c]pyrazol-3-olate;
sodium 2-[4-(pyridin-3-ylmethoxy)pyridin-2-yl]-2,6-dihydro-4H-thieno[3,4-c]pyrazol-3-olate;
methyl 2-{5-[ethyl(phenyl)sulfamoyl]pyridin-2-yl}-3-oxo-1,2,3,4,6,7-hexahydro-5H-pyrazolo[4,3-c]pyridine-5-carboxylate;
cyclopentyl 6-(3-oxo-4,6-dihydro-1H-thieno[3,4-c]pyrazol-2(3H)-yl)pyridine-3-carboxylate;
2-methylpropyl 6-(3-oxo-4,6-dihydro-1H-thieno[3,4-c]pyrazol-2(3H)-yl)pyridine-3-carboxylate;
2-[4-(propan-2-yl)pyridin-2-yl]-1,2,4,6-tetrahydro-3H-thieno[3,4-c]pyrazol-3-one;
sodium 2-[5-(propan-2-yl)pyridin-2-yl]-2,6-dihydro-4H-thieno[3,4-c]pyrazol-3-olate;
methyl 2-{5-[ethyl(phenyl)sulfamoyl]pyridin-2-yl}-3-oxo-2,3,4,6-tetrahydro-1H-thieno[3,4-c]pyrazole-4-carboxylate;
propan-2-yl 6-(3-oxo-4,6-dihydro-1H-thieno[3,4-c]pyrazol-2(3H)-yl)pyridine-3-carboxylate;
sodium 2-{5-[ethyl(phenyl)sulfamoyl]pyridin-2-yl}-6-methoxy-2,4,5,6-tetrahydrocyclopenta[c]pyrazol-3-olate;
N-ethyl-6-(3-oxo-3,4,5,6-tetrahydrocyclopenta[c]pyrazol-2(1H)-yl)-N-phenylpyridine-3-sulfonamide;
sodium 2-[4-(pyridin-3-ylmethoxy)pyridin-2-yl]-2,6-dihydro-4H-thieno[3,4-c]pyrazol-3-olate;
2,2-dimethylpropyl 6-(3-oxo-4,6-dihydro-1H-thieno[3,4-c]pyrazol-2(3H)-yl)pyridine-3-carboxylate;
2-[5-(5-tert-butyl-1,2,4-oxadiazol-3-yl)pyridin-2-yl]-1,2,4,6-tetrahydro-3H-thieno[3,4-c]pyrazol-3-one;
N-cyclopentyl-N-methyl-6-(3-oxo-4,6-dihydro-1H-thieno[3,4-c]pyrazol-2(3H)-yl)pyridine-3-sulfonamide;
N-cyclopentyl-N-ethyl-6-(3-oxo-3,4,5,6-tetrahydrocyclopenta[c]pyrazol-2(1H)-yl)pyridine-3-sulfonamide;
N-cyclopentyl-N-(2,3-dihydroxypropyl)-6-(3-oxo-4,6-dihydro-1H-thieno[3,4-c]pyrazol-2(3H)-yl)pyridine-3-sulfonamide;
2,2-dimethylpropyl 6-[5-(methylsulfonyl)-3-oxo-1,3,4,5,6,7-hexahydro-2H-pyrazolo[4,3-c]pyridin-2-yl]pyridine-3-carboxylate;
2-[5-(3-tert-butyl-1,2,4-oxadiazol-5-yl)pyridin-2-yl]-1,2,4,6-tetrahydro-3H-thieno[3,4-c]pyrazol-3-one.

In the text hereinbelow, the term "protecting group" (PG) means a group that can, firstly, protect a reactive function such as an alcohol or an amine during a synthesis. Examples of protecting groups and of protection and deprotection methods are given in "Protective Groups in Organic Synthesis", Greene et al., 3rd edition (John Wiley & Sons, Inc., New York).

In the text hereinbelow, the term "leaving group" (LG) means a nucleofugal group that can be readily cleaved from a molecule by breaking a heterolytic bond, with loss of an electron pair. This group may thus be readily replaced with another nucleophilic group during a substitution reaction, for example. Such leaving groups are, for example, halogens or an activated hydroxyl group such as a mesyl, tosyl, triflate, acetyl, etc. group. Examples of leaving groups and of references for preparing them are given in "Advances in Organic chemistry", J. March, 3rd edition, Wiley Interscience, pp. 310-316.

In accordance with the invention, the compounds of general formula (I) may be prepared according to the process that follows, illustrated in Scheme 1.

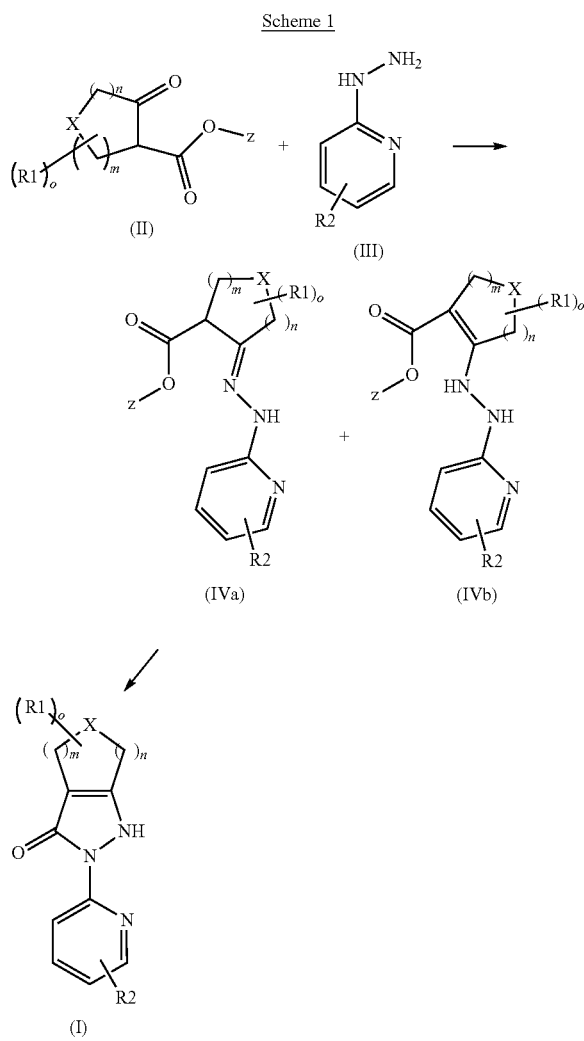

The synthesis of the compounds of general formula (I) is performed starting with the compounds of formula (II), in which R1, X, n, m and o are as described previously and z represents an alkyl group, preferentially methyl or ethyl, which is condensed in a protic solvent of alcohol type, preferably methanol, at a temperature of between 20 and 60° C., with a compound of formula (III) in which R2 is as described previously, to give an intermediate of formula (IV) that is in the form of a compound of formula (IVa) or (IVb), or a mixture of the two, and which is cyclized in the presence of an organic base, preferably sodium methoxide, in a protic solvent such as methanol, at a temperature of between 20 and 50° C.

The compounds (I) obtained are optionally converted with the corresponding acid or base into the salt.

When their preparation method is not described, the compounds of formula (II) are commercially available or described in the literature, or alternatively may be prepared according to methods that are known to those skilled in the art.

Schemes 2a, 2b and 2c describe the preparation of the compounds of formula (III).

The compounds of formula (III) are obtained from the compound of formula (V), with LG and R2 as defined previously, via addition of hydrazine hydrate, preferably in a protic solvent such as ethanol, at a temperature of between 60 and 80° C. (Scheme 2a).

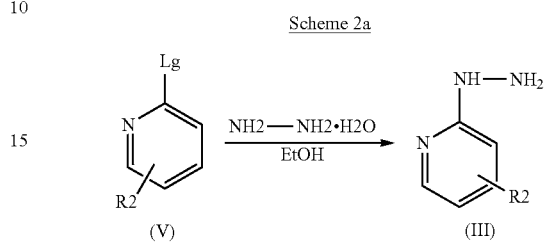

The compounds of formula (III) may also be obtained in two steps starting with the compound of formula (V). The hydrazine function is then introduced, via a coupling reaction between benzophenone hydrazone of formula (VI) and the compound of formula (V) in the presence of a catalytic amount of palladium, to give the intermediate of formula (VII), the hydrazine function of which is freed by acidic treatment, such as hydrochloric acid, preferably at a concentration of between 6 and 12 N, in a binary mixture of immiscible solvents such as toluene and water at a temperature of 100° C. (Scheme 2b).

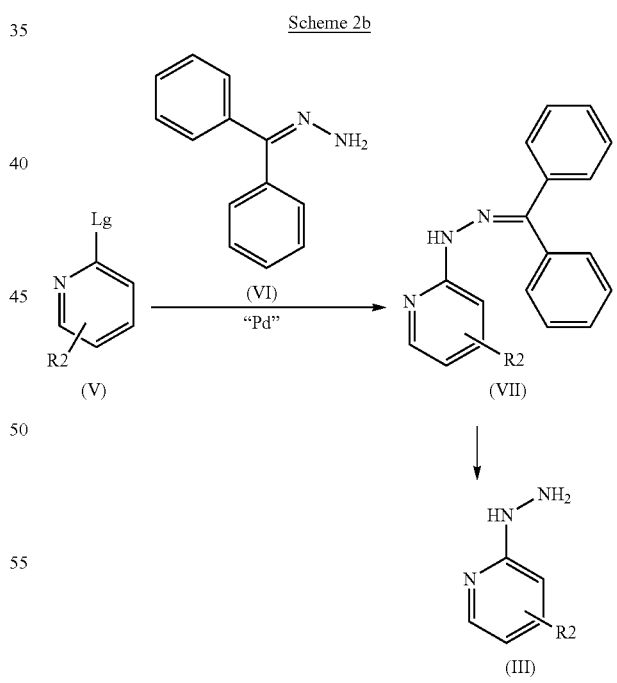

Alternatively, the compounds of formula (III) may be synthesized from an amino pyridine of formula (VIII) with R2 as defined previously, via the action of a mixture of nitric acid and concentrated sulfuric acid at 0° C. to obtain the N-nitroamine intermediate, which is reduced in 10N sodium hydroxide in the presence of zinc (Scheme 2c).

Scheme 2c

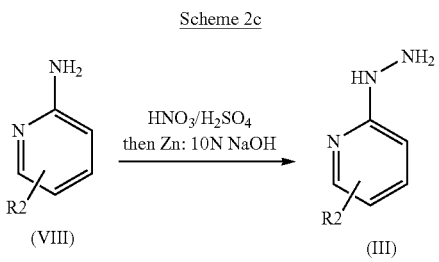

In the preceding schemes, the starting compounds, intermediates and reagents, when their preparation method is not described, are commercially available or described in the literature, or else may be prepared according to methods known to those skilled in the art.

According to another of its aspects, a subject of the invention is also the compounds of formulae (IVa) and (IVb). These compounds are useful as intermediates for synthesizing the compounds of formula (I).

EXAMPLES

The examples that follow illustrate the preparation of certain compounds in accordance with the invention. The numbers of the compounds presented as examples refer to those in the table given later, which illustrates the chemical structures and physical properties of a few compounds according to the invention.

The abbreviations and semi-structural formulae below are used:
EtOAc Ethyl acetate
AcOH Acetic acid
anh. Anhydrous
TLC Thin-layer chromatography
LC Liquid chromatography
Cs$_2$CO$_3$ Caesium carbonate
DCM Dichloromethane
DMF Dimethylformamide
DMSO Dimethyl sulfoxide
DME 1,2-Dimethoxyethane
EtOH Ethanol
MeOH Methanol
h Hour(s)
HCl Hydrochloric acid
K$_2$CO$_3$ Potassium carbonate
NH$_4$Cl Ammonium chloride
NaHCO$_3$ Sodium hydrogen carbonate
Na$_2$SO$_4$ Sodium sulfate
MS Mass spectrometry
TEA Triethylamine
TFA Trifluoroacetic acid
THF Tetrahydrofuran
RT Room temperature
HNO$_3$ Nitric acid
H$_2$SO$_4$ Sulfuric acid
Conc. Concentrated
racBINAP (±)-2,2-Bis(diphenylphosphino)-1,1'binaphthalene
TBTU 2-(1-H-Benzotriazol-1-yl)-1,1,3,3-tetramethyluronium tetrafluoroborate
DIEA Diisopropylethylamine
NMO 4-Methylmorpholine N-oxide
OsO4 Osmium tetroxide
pTsOH para-Toluenesulfonic acid
Tr Retention time
T Time
T° C. Temperature in ° C.
Min Minutes
m.p. Melting point The proton magnetic resonance (1H NMR) spectra, as described below, are recorded at 400 MHz in DMSO-d6, using the peak of DMSO-d5 as reference. The chemical shifts δ are expressed in parts per million (ppm). The signals observed are expressed as follows: s=singlet; bs=broad singlet; d=doublet; dd=doublet of doublets; dt=doublet of triplets; t=triplet; m=multiplet; H=proton.

The mass spectra are obtained under the following LC/MS coupling conditions:

Method 1: Column: Jsphere 33×2 mm; 4 μM;

Eluents: A=H$_2$O+0.05% TFA; B=CH$_3$CN+0.05% TFA

T0: 98% A; T1.0 to T5.0 min: 95% B;

Method 2: Column: Acquity BEH C18 (50×2.1 mm; 1.7 μM); 220 nm

Eluents: A=H$_2$O+0.05% TFA; B=CH$_3$CN+0.035% TFA.

T0: 98% A; T1.6 to T2.1 min: 100% B; T2.5 to T3 min: 98% A flow rate 1.0 mL/min-T° C.=40° C., injection 2 μL Example 1

2-pyridin-2-yl-1,2,4,6-tetrahydro-3H-thieno[3,4-c]Pyrazol-3-one (Compound 1 of Table I)

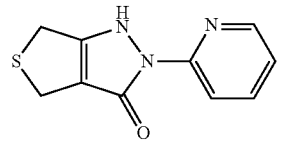 [SMILES: O=c1c2c([nH]n1-c1ccccn1)CSC2]

A mixture of 7 g (64.1 mmol) of 2-hydrazinopyridine and 10.3 g (64.1 mmol) of methyl 4-oxotetrahydrothiophene-3-carboxylate in 130 mL of MeOH is heated for 12 hours at 80° C. The medium is then concentrated under reduced pressure and the residue obtained is purified by chromatography on a column of silica gel, eluting with a DCM/MeOH gradient of from 0 to 10% MeOH. After concentrating under reduced pressure, 8.7 g (34.5 mmol) of hydrazone intermediate, in the form of a yellow powder, are isolated and are then added portionwise, at room temperature, to a solution of 0.8 g (34.5 mmol) of sodium in 46 mL of anhydrous MeOH. The reaction medium is stirred for 2 hours at room temperature, and the precipitate formed is then filtered off and washed successively with 10 mL of MeOH and 20 mL of pentane. The residue obtained is dissolved in 20 mL of water and 10 mL of acetic acid are added. The precipitate obtained is filtered off, washed with 10 mL of water, dried under vacuum and recrystallized from EtOH. 4.2 g of 2-pyridin-2-yl-1,2,4,6-tetrahydro-3H-thieno[3,4-c]pyrazol-3-one are obtained in the form of a whitish powder.

Yield=56% m.p. (° C.)=152

M=C$_{10}$H$_9$N$_3$OS=219; M+H=220; Method 2: Tr=0.81 min.

$^1$H NMR, d6-DMSO, 400 MHz, δ (ppm): 8.45 (d, 1H); 8.2 (d, 1H); 7.95 (m, 1H); 7.3 (t, 1H); 4.0 (s, 2H); 3.8 (s, 2H).

Example 2

2-[4-(Dimethylamino)Pyridin-2-yl]-1,2,4,6-tetrahydro-3H-thieno[3,4-c]Pyrazol-3-one Hydrochloride (Compound 56 of Table II)

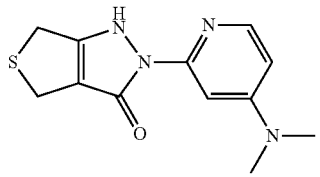 [SMILES: CN(C)c1ccnc(-n2[nH]c3c(c2=O)CSC3)c1]

2.1. 2-bromo-N,N-dimethylpyridin-4-amine

To a solution of 12.6 mL (125 mmol) of N,N-dimethylethanolamine in 160 mL of anhydrous hexane are added, under an argon atmosphere, at −5° C., over 2 hours 30 minutes, 100 mL (250 mmol) of 2.5 M n-butyllithium in hexane, and the reaction medium is then stirred for 30 minutes at 0° C., followed by addition of 7.6 g (62.5 mmol) of 4-dimethylaminopyridine. After stirring for 1 hour at 0° C., the reaction medium is cooled to −78° C. and 51.8 g (156.2 mmol) of carbon tetrabromide dissolved in 250 mL of anhydrous hexane are added over 2 hours 30 minutes at −78° C. The temperature is allowed to rise to 0° C. and stirring is then continued for 1 hour 30 minutes.

The medium is then hydrolysed with water (400 mL) and subsequently extracted with Et$_2$O (400 mL) and DCM (2×400 mL). The combined organic phases are dried over Na$_2$SO$_4$, filtered and concentrated under reduced pressure. 6.4 g of 2-bromo-N,N-dimethylpyridin-4-amine are obtained in the form of a brown solid, which is used without further purification in the following step.

Yield=51%

$^1$H NMR, (CDCl$_3$, 400 MHz, δ (ppm): 7.9 (d, 1H); 6.6 (s, 1H); 6.4 (d, 1H); 2.9 (s, 6H).

2.2. 2-[2-(diphenylmethylidene)Hydrazino]-N,N-dimethylpyridin-4-amine

To a mixture of 3.3 g (16.41 mmol) of 2-bromo-N,N-dimethylpyridin-4-amine in 40 mL of anhydrous toluene, 3.5 g (18.05 mmol) of benzophenone hydrazone, 2.2 g (23 mmol) of anhydrous sodium tert-butoxide and 100 mg (0.82 mmol) of benzeneboronic acid in 40 mL of toluene are added, under argon, at room temperature, after having degassed the reaction medium under argon, 74 mg (0.33 mmol) of palladium acetate and 205 mg (0.33 mmol) of racBINAP. The reaction medium is then heated for 4 hours at 80° C. The reaction medium is taken up in 200 mL of EtOAc, washed successively with water (3×30 mL), with saturated NaHCO$_3$ solution (30 mL) and with brine (30 mL) and then dried over Na$_2$SO$_4$, filtered and concentrated under reduced pressure. The residue obtained is purified by chromatography on a column of silica gel, eluting with a DCM/MeOH gradient of from 0 to 10% MeOH. After concentrating under reduced pressure, 4.5 g of 2-[2-(diphenylmethylidene)hydrazino]-N,N-dimethylpyridin-4-amine are obtained in the form of a red solid.

Yield=87%

2.3. 2-hydrazino-N,N-dimethylpyridin-4-amine

A mixture of 4.5 g (14.22 mmol) of 2-[2-(diphenylmethylidene)hydrazino]-N,N-dimethylpyridin-4-amine in 300 mL of toluene and 80 mL of aqueous 37% hydrochloric acid is heated for 4 hours at 110° C. After cooling to room temperature, the reaction medium is extracted with toluene (3×300 mL). The aqueous phase is diluted with 200 mL of water, neutralized at 0° C. by adding 12N sodium hydroxide solution, and then extracted with DCM (3×150 mL). The organic phases are combined, washed with brine (300 mL) and then dried over Na$_2$SO$_4$, filtered and concentrated under reduced pressure. 1.87 g of 2-hydrazino-N,N-dimethylpyridin-4-amine are obtained in the form of a brown solid, which is used without further purification in the following step.

Yield=87%

$^1$H NMR (ppm, d6-DMSO, 400 MHz): 7.6 (d, 1H); 6.9 (s, 1H); 6.1 (dd, 1H); 5.9 (d, 1H); 4 (bs, 2H); 2.9 (s, 6H).

2.4. 2-[4-(Dimethylamino)Pyridin-2-yl]-1,2,4,6-tetrahydro-3H-thieno[3,4-c]Pyrazol-3-one Hydrochloride According to the process described in Example 1, starting with 1.87 g of 2-hydrazino-N,N-dimethylpyridin-4-amine and 1.97 g of methyl 4-oxotetrahydrothiophene-3-carboxylate, 35 mg of 2-[4-(dimethylamino)pyridin-2-yl]-1,2,4,6-tetrahydro-3H-thieno[3,4-c]pyrazol-3-one are obtained. The hydrochloride is prepared by freeze-drying the 35 mg obtained previously, dissolved in 1 mL of 0.1N HCl.

36 mg of 2-[4-(dimethylamino)pyridin-2-yl]-1,2,4,6-tetrahydro-3H-thieno[3,4-c]pyrazol-3-one hydrochloride are thus obtained in the form of a white lyophilizate.

Yield=1% m.p. (° C.)=182

M=C$_{12}$H$_{14}$N$_4$OS=262; M+H=263; Method 2: Tr=0.59 min.

$^1$H NMR, d6-DMSO, 400 MHz, δ (ppm): 7.7 (d, 1H); 6.9 (s, 1H); 6.6 (d, 1H); 3.2 (s, 2H); 3.5 (s, 2H); 2.9 (s, 6H).

Example 3

2-(4-methoxypyridin-2-yl)-1,2,4,6-tetrahydro-3H-thieno[3,4-c]Pyrazol-3-one (Compound 55 of Table II)

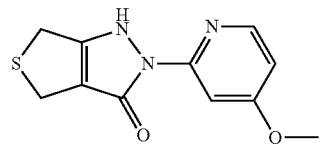 [SMILES: COc1ccnc(-n2[nH]c3c(c2=O)CSC3)c1]

3.1. 2-[2-(Diphenylmethylidene)Hydrazino]-4-methoxypyridine

According to the process described in Example 2.2, starting with 0.5 g of 2-chloro-4-methoxypyridine and 0.75 g of benzophenone hydrazone, 0.76 g of 2-[2-(diphenylmethylidene)hydrazino]-4-methoxypyridine is obtained in the form of a yellow solid, which is used without further purification in the following step.

Yield=73%

¹H NMR, CDCl₃, 400 MHz, δ (ppm): 8.2 (s, 1H); 7.9 (d, 1H); 7.7-7.5 (m, 5H); 7.4-7.2 (m, 5H); 7.1 (s, 1H); 6.4 (d, 1H); 3.9 (s, 3H).

3.2. 2-hydrazino-4-methoxypyridine

According to the process described in Example 2.3, starting with 0.76 g of 2-[2-(diphenylmethylidene)hydrazino]-4-methoxypyridine, 0.24 g of 2-hydrazinomethoxypyridine is obtained in the form of a yellow lyophilizate, which is used without further purification in the following step.

Yield=69%

¹H NMR, d6-DMSO, 400 MHz, δ (ppm): 9.7 (bs, 1H); 7.7 (d, 1H); 6.5 (d, 1H); 6.4 (s, 1H); 4.8 (bs, 2H); 3.9 (s, 3H).

3.3. 2-(4-methoxypyridin-2-yl)-1,2,4,6-tetrahydro-3H-thieno[3,4-c]Pyrazol-3-one According to the process described in Example 1, starting with 243 mg of 2-hydrazino-4-methoxypyridine and 280 mg of methyl 4-oxotetrahydrothiophene-3-carboxylate, 82 mg of 2-(4-methoxypyridin-2-yl)-1,2,4,6-tetrahydro-3H-thieno[3,4-c]pyrazol-3-one are obtained in the form of a white solid.

Yield=40% m.p. (° C.)=254

M=C₁₁H₁₁N₃O₂S=249; M+H=250; Method 2: Tr=0.8 min.

¹H NMR, d6-DMSO, 400 MHz, δ (ppm): 8.1 (d, 1H); 8.05 (d, 1H); 6.05 (d, 1H); 3.8 (s, 3H); 3.7 (s, 2H); 3.6 (s, 2H)

Example 4

N-methyl-6-(3-oxo-4,6-dihydro-1H-thieno[3,4-c]Pyrazol-2(3H)-yl)-N-pyridin-2-ylpyridine-3-sulfonamide (Compound 21 of Table I)

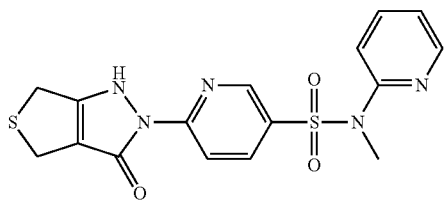 [SMILES: CN(c1ccccn1)S(=O)(=O)c1ccc(-n2[nH]c3c(c2=O)CSC3)nc1]

4.1. 6-chloro-N-methyl-N-pyridin-2-ylpyridine-3-sulfonamide

To a solution of 1.3 g (11.8 mmol) of N-methylpyridin-2-amine in 25 mL of DCM are added, at 0° C., 3.3 mL (23.6 mmol) of triethylamine and then, portionwise, 2.5 g (11.8 mmol) of 6-chloropyridine-3-sulfonyl chloride (prepared according to document WO 98/40332). After stirring for 12 hours at room temperature, the reaction medium is taken up in 100 mL of DCM, washed successively with 100 mL of water and 30 mL of brine, dried over Na₂SO₄, filtered and concentrated under reduced pressure. The residue obtained is purified by chromatography on a column of silica gel, eluting with a 4/1 cyclohexane/EtOAc mixture. After concentrating under reduced pressure, 2.8 g of 6-chloro-N-methyl-N-pyridin-2-ylpyridine-3-sulfonamide are obtained in the form of a brown solid.

Yield=84%

¹H NMR, CDCl₃, 400 MHz, δ (ppm): 8.5 (s, 1H); 8.25 (d, 1H); 7.8 (dd, 1H); 7.7 (t, 1H); 7.5 (d, 1H); 7.3 (d, 1H); 7.15 (t, 1H); 3.2 (s, 3H).

4.2. 6-hydrazino-N-methyl-N-pyridin-2-ylpyridine-3-sulfonamide

A solution of 1.4 g (4.9 mmol) of 6-chloro-N-methyl-N-pyridin-2-ylpyridine-3-sulfonamide and 0.96 mL (19.7 mmol) of hydrazine monohydrate in 8 mL of EtOH is heated for 12 hours at 80° C. The precipitate obtained, after cooling to room temperature, is filtered off, washed with 10 mL of EtOH and then dried under vacuum. 0.85 g of 6-hydrazino-N-methyl-N-pyridin-2-ylpyridine-3-sulfonamide is obtained in the form of pale yellow crystals.

Yield=62%.

¹H NMR, CDCl₃, 400 MHz, δ (ppm): 8.35 (s, 2H); 8.7 (m, 2H); 7.5 (d, 1H); 7.15 (dd, 1H); 6.7 (d, 1H); 6.4 (bs, 1H); 3.5-4.0 (bs, 2H); 3.3 (s, 3H).

4.3. N-methyl-6-(3-oxo-4,6-dihydro-1H-thieno[3,4-c]Pyrazol-2(3H)-yl)-N-pyridin-2-ylpyridine-3-sulfonamide According to the process described in Example 1, starting with 476 mg of 6-hydrazino-N-methyl-N-pyridin-2-ylpyridine-3-sulfonamide and 273 mg of methyl 4-oxotetrahydrothiophene-3-carboxylate, 416 mg of N-methyl-6-(3-oxo-4,6-dihydro-1H-thieno[3,4-c]pyrazol-2(3H)-yl)-N-pyridin-2-ylpyridine-3-sulfonamide are obtained in the form of a white solid.

Yield=45% m.p. (° C.)=226

M=C₁₆H₁₅N₅O₃S₂=389; M+H=390; Method 2: Tr=0.98 min.

¹H NMR, d6-DMSO, 400 MHz, δ (ppm): 12.0 (bs, 1H); 8.6 (s, 1H); 8.5 (bs, 1H); 8.4 (d, 1H); 8.2 (dd, 1H); 7.55 (d, 1H); 7.3 (t, 1H); 4.0 (s, 2H); 3.8 (s, 2H); 3.3 (s, 3H).

Example 5

N-ethyl-6-(3-oxo-3,5,6,7-tetrahydrothiopyrano[3,2-c]Pyrazol-2(1H)-yl)-N-phenylpyridine-3-sulfonamide (Compound 24 of Table I)

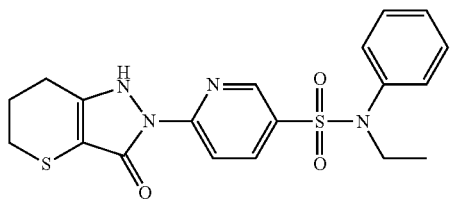 [SMILES: CCN(c1ccccc1)S(=O)(=O)c1ccc(-n2[nH]c3c(c2=O)SCCC3)nc1]

5.1. Ethyl 3-oxotetrahydro-2H-thiopyran-2-carboxylate

To a solution of 5 g (219 mmol) of sodium in 13 mL of anhydrous EtOH and 88 mL of ether are added dropwise, at 0° C. and under argon, 20.5 g (87.5 mmol) of ethyl 4-[(2-ethoxy- 2-oxoethyl)sulfanyl]butanoate. After stirring for 18 hours at room temperature, the reaction mixture is poured into a mixture of AcOH (12 mL)/ice (70 g). The medium is then concentrated under reduced pressure, and the residue obtained is taken up in 100 mL of ether, washed with brine (2×50 mL), dried over $Na_2SO_4$, filtered and concentrated under reduced pressure. The residue obtained is purified by chromatography on silica gel, eluting with a cyclohexane/EtOAc gradient of from 0 to 10% EtOAc. 5.64 g of ethyl 3-oxotetrahydro-2H-thiopyrane-2-carboxylate are obtained in the form of a yellow oil.

Yield=34%.

$^1$H NMR, $CDCl_3$, 400 MHz, δ (ppm): 12.3 (s, 1H); 4.3 (q, 2H); 2.80 (m, 2H); 2.4 (t, 2H); 2.15 (m, 2H); 1.4 (t, 3H).

5.2. N-ethyl-6-(3-oxo-3,5,6,7-tetrahydrothiopyrano[3,2-c]Pyrazol-2(1H)-yl)-N-phenylpyridine-3-sulfonamide A mixture of 1 g (5.31 mmol) of ethyl 3-oxotetrahydro-2H-thiopyrane-2-carboxylate and 1.55 g of 6-hydrazino-N-methyl-N-pyridin-2-ylpyridine-3-sulfonamide in 10 mL of MeOH is heated for 15 hours at 80° C. After cooling to room temperature, the precipitate obtained is filtered off and washed with 5 mL of MeOH, and then recrystallized from EtOH. 395 mg of N-ethyl-6-(3-oxo-3,5,6,7-tetrahydrothiopyrano[3,2-c]pyrazol-2(1H)-yl)-N-phenylpyridine-3-sulfonamide are obtained in the form of a white powder.

Yield=16%
m.p. (° C.)=198
M=$C_{19}H_{20}N_4O_3S_2$=416; M+H=417; Method 2: Tr=1.12 min
$^1$H NMR, d6-DMSO, 400 MHz, δ (ppm): 11.9 (bs, 1H); 8.6 (bs, 1H); 8.5 (s, 1H); 8.1 (d, 1H); 7.4 (m, 3H); 7.1 (d, 2H); 3.6 (q, 2H); 3.0 (t, 2H); 2.6 (t, 2H); 2.0 (q, 2.0); 1.0 (t, 3H).

Example 6

Tert-butyl 2-[5-[Ethyl(Phenyl)Sulfamoyl]Pyridin-2-yl]-3-oxo-1,2,3,4,6,7-hexahydro-5H-pyrazolo[4,3-c]Pyridine-5-carboxylate (Compound 28 of Table I)

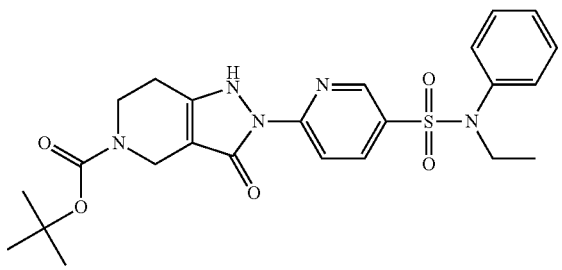 [SMILES: CCN(c1ccccc1)S(=O)(=O)c1ccc(-n2[nH]c3c(c2=O)CN(C(=O)OC(C)(C)C)CC3)nc1]

6.1. 1-tert-butyl-3-methyl-4-oxopiperidine 1,3-dicarboxylate

To a mixture of 10 g (51.6 mmol) of methyl 4-oxopiperidine-3-carboxylate and 7.3 mL (51.6 mmol) of triethylamine in 100 mL of DCM are added 11.3 g (51.6 mmol) of di-tert-butyl dicarbonate. After 2 hours at room temperature, the medium is taken up in 300 mL of DCM, washed with 200 mL of water, dried over $Na_2SO_4$ and then filtered and concentrated under reduced pressure. 13 g of 1-tert-butyl-3-methyl-4-oxopiperidine 1,3-dicarboxylate are obtained in the form of a white solid, which is used without further purification in the following step.

6.2. Tert-butyl 2-[5-[Ethyl(Phenyl)Sulfamoyl]Pyridin-2-yl]-3-oxo-1,2,3,4,6,7-hexahydro-5H-pyrazolo[4,3-c]Pyridine-5-carboxylate According to the process described in Example 1, starting with 1.7 g of 6-hydrazino-N-methyl-N-pyridin-2-ylpyridine-3-sulfonamide and 1.5 g of 1-tert-butyl-3-methyl-4-oxopiperidine 1,3-dicarboxylate, 190 mg of tert-butyl 2-[5-[ethyl(phenyl)sulfamoyl]pyridin-2-yl]-3-oxo-1,2,3,4,6,7-hexahydro-5H-pyrazolo[4,3-c]pyridine-5-carboxylate are obtained in the form of a white solid.

Yield=16%
m.p. (° C.)=192
M=$C_{24}H_{29}N_5O_5S$=499; M+H=500; Method 2: Tr=1.23 min
$^1$H NMR, d6-DMSO, 400 MHz, δ (ppm): 12.1 (bs, 1H); 8.6 (bs, 1H); 8.5 (s, 1H); 8.1 (dd, 1H); 7.4 (m, 3H); 7.1 (d, 2H); 4.1 (s, 2H); 3.6 (m, 4H); 2.7 (m, 2H); 1.4 (s, 9H); 1.0 (t, 3H).

Example 7

N-ethyl-6-(3-oxo-1,4,6,7-tetrahydropyrano[4,3-c]Pyrazol-2(3H)-yl)-N-phenylpyridine-3-sulfonamide (Compound 25 of Table I)

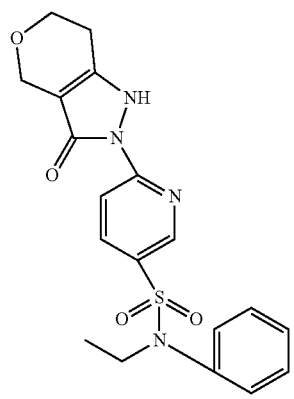 [SMILES: CCN(c1ccccc1)S(=O)(=O)c1ccc(-n2[nH]c3c(c2=O)COCC3)nc1]

7.1. Propyl 4-oxotetrahydro-2H-pyran-3-carboxylate

The compound is prepared according to the procedure described in JACS Vol. 119, No. 18, pp. 4285-4291.

7.2. N-ethyl-6-(3-oxo-1,4,6,7-tetrahydropyrano[4,3-c]Pyrazol-2(3H)-yl)-N-phenylpyridine-3-sulfonamide According to the process described in Example 1, starting with 0.47 g of 6-hydrazino-N-methyl-N-pyridin-2-ylpyridine-3-sulfonamide and 0.3 g of propyl 4-oxotetrahydro-2H-pyran-3-carboxylate, 370 mg of N-ethyl-6-(3-oxo-1,4,6,7-tetrahydropyrano[4,3-c]pyrazol-2(3H)-yl)-N-phenylpyridine-3-sulfonamide are obtained in the form of a white powder.

Yield=57%
m.p. (° C.)=164
M=$C_{19}H_{20}N_4O_4S$=400; M+H=401; Method 2: Tr=1.0 min ¹H NMR, d6-DMSO, 400 MHz, δ (ppm): 12.0 (bs, 1H); 8.6 (d, 1H); 8.4 (s, 1H); 8.0 (d, 1H); 7.4 (m, 3H); 7.1 (m, 2H); 4.3 (s, 2H); 3.85 (t, 2H); 3.6 (q, 2H); 2.6 (t, 2H); 1.0 (t, 3H).

Example 8

Sodium 4-benzyl-2-{(5-[Ethyl(Phenyl)Sulfamoyl] Pyridin-2-yl}-5-oxo-4,5,6,7-tetrahydro-2H-pyrazolo [4,3-b]Pyridin-3-olate (Compound 35 of Table I)

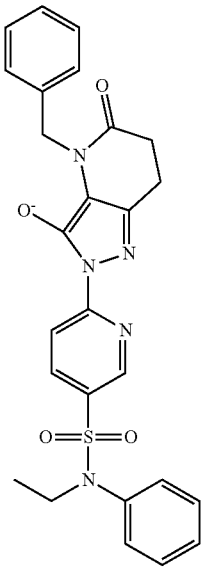 [SMILES: CCN(c1ccccc1)S(=O)(=O)c1ccc(-n2nc3c(c2[O-])N(Cc2ccccc2)C(=O)CC3)nc1]

According to the process described in Example 1, starting with 0.8 g of 6-hydrazino-N-methyl-N-pyridin-2-ylpyridine-3-sulfonamide and 0.76 g of ethyl 1-benzyl-3,6-dioxopiperidine-2-carboxylate obtained according to Tetrahedron, Vol. 40, No. 13 p. 2505, 220 mg of the expected compound are obtained in the form of a white solid, which is taken up in 6 mL of a water/CH₃CN mixture (5/1) and 1 eq. of 1N NaOH, and then freeze-dried. 225 mg of sodium 4-benzyl-2-{5-[ethyl(phenyl)sulfamoyl]pyridin-2-yl}-5-oxo-4,5,6,7-tetrahydro-2H-pyrazolo[4,3-b]pyridin-3-olate are thus obtained in the form of a white lyophilizate.

Yield=12%
m.p. (° C.)>250
M=$C_{26}H_{25}N_5O_4S$=503; M+H=504; Method 2: Tr=1.16 min.
¹H NMR, d6-DMSO, 400 MHz, δ (ppm): 8.7 (d, 1H); 8.4 (s, 1H); 7.8 (d, 1H); 7.5-7.1 (m, 10H); 4.7 (s, 2H); 4.2 (s, 2H); 3.6 (q, 2H); 3.1 (s, 2H); 1.0 (t, 3H).

Example 9

Sodium 2-(4-ethylpyridin-2-yl)-2,6-dihydro-4H-thieno[3,4-c]Pyrazol-3-olate (Compound 57 of Table II)

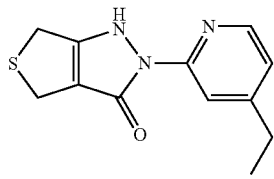 [SMILES: CCc1ccnc(-n2[nH]c3c(c2=O)CSC3)c1]

9.1. 4-ethyl-2-hydrazinopyridine

To a solution of 5 g (40.9 mmol) of 4-ethylpyridin-2-amine in 10 mL of concentrated $H_2SO_4$ at 0° C. are added 8 mL of an $H_2SO_4$/$HNO_3$ mixture (1/1) at a temperature of between 0 and 10° C., and stirring is maintained for 1 hour at 0° C. The reaction medium is then poured onto 100 g of ice and the white precipitate obtained is filtered off and washed successively with 10 mL of water, 10 mL of $Et_2O$ and 10 mL of pentane. The solid obtained is taken up in 100 mL of 10N NaOH at 0° C., 7.76 g (187 mmol) of zinc powder are added and the reaction medium is then stirred for 3 hours at 0° C. The reaction medium is then filtered through Celite and the filtrate is extracted with EtOAc (3×200 mL). The organic phases are combined, dried over $Na_2SO_4$, filtered and then concentrated under reduced pressure. 4.3 g of 4-ethyl-2-hydrazinopyridine are obtained in the form of a red oil, which is used without further purification in the following step.

Yield=77%
¹H NMR, CDCl₃, 400 MHz, δ (ppm): 7.9 (d, 1H); 7.2 (bs, 1H); 6.5 (s, 1H); 6.4 (d, 1H); 4.1 (s, 2H); 2.5 (q, 2H); 1.1 (t, 3H).

9.2. Sodium 2-(4-ethylpyridin-2-yl)-2,6-dihydro-4H-thieno[3,4-c]pyrazol-3-olate

According to the process described in Example 8, starting with 0.88 g of 4-ethyl-2-hydrazinopyridine and 1.0 g of methyl 4-oxotetrahydrothiophene-3-carboxylate, 225 mg of sodium 2-(4-ethylpyridin-2-yl)-2,6-dihydro-4H-thieno[3,4-c]pyrazol-3-olate are obtained in the form of a white lyophilizate.

Yield=15%
m.p. (° C.)>260° C.
M=$C_{12}H_{13}N_3OS$=247; M+H=248; Method 2: Tr=1.05 min.
¹H NMR, d6-DMSO, 400 MHz, δ (ppm): 8.2 (s, 1H); 8.1 (d, 1H); 6.7 (d, 1H); 3.7 (s, 2H); 3.5 (s, 2H); 2.5 (q, 2H); 1.1 (t, 3H).

Example 10

Sodium 2-{(5-[tert-butyl(Methyl)Sulfamoyl]Pyridin-2-yl}-2,6-dihydro-4H-thieno[3,4-c]Pyrazol-3-olate (Compound 36 of Table I)

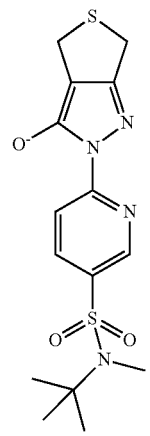 [SMILES: CN(C(C)(C)C)S(=O)(=O)c1ccc(-n2nc3c(c2[O-])CSC3)nc1]

10.1. N-tert-butyl-6-chloropyridine-3-sulfonamide

According to the process described in Example 4.1, starting with 2 g (9.43 mmol) of 6-chloropyridine-3-sulfonyl chloride and 0.99 mL (9.43 mmol) of tert-butylamine, 1.91 g of N-tert-butyl-6-chloropyridine-3-sulfonamide are obtained in the form of a white solid.

Yield=82%

$^1$H NMR, CDCl$_3$, 400 MHz, δ (ppm): 8.8 (d, 1H); 8 (dd, 1H); 7.4 (d, 1H); 4.5 (bs, 1H); 1.2 (s, 9H).

10.2. N-tert-butyl-6-chloro-N-methylpyridine-3-sulfonamide

A mixture of 0.97 g (3.9 mmol) of N-tert-butyl-6-chloropyridine-3-sulfonamide, 2.43 mL (39 mmol) of methyl iodide and 5.4 g (39 mmol) of K$_2$CO$_3$ in 40 mL of acetone is refluxed for 12 hours. The reaction medium is filtered at room temperature, and the filtrate is concentrated under reduced pressure. The residue obtained is purified on silica gel, eluting with a cyclohexane/EtOAc gradient of from 0 to 20% EtOAc, to give 0.66 g of N-tert-butyl-6-chloro-N-methylpyridine-3-sulfonamide in the form of a yellow solid.

Yield=65%

$^1$H NMR, CDCl$_3$, 400 MHz, δ (ppm): 8.8 (d, 1H); 8 (dd, 1H); 7.4 (d, 1H); 3 (s. 3H); 1.4 (s, 9H).

10.3. N-tert-butyl-6-hydrazino-N-methylpyridine-3-sulfonamide

According to the process described in Example 4.2, starting with 0.66 g (2.53 mmol) of N-tert-butyl-6-chloro-N-methylpyridine-3-sulfonamide and 0.46 mL of hydrazine monohydrate, 0.55 g of N-tert-butyl-6-hydrazino-N-methylpyridine-3-sulfonamide is obtained in the form of a white solid, which is used without further purification in the following step.

Yield=84%

$^1$H NMR, CDCl$_3$, 400 MHz, δ (ppm): 8.8 (d, 1H); 8 (dd, 1H); 7 (d, 1H); 6.6 (bs, 1H); 4.1 (bs, 2H); 3.1 (s, 3H); 1.5 (s, 9H).

10.4. Sodium 2-{5-[tert-butyl(Mmethyl)Sulfamoyl] Pyridin-2-yl}-2,6-dihydro-4H-thieno[3,4-c]Pyrazol-3-olate According to the process described in Example 8, starting with 0.55 g of N-tert-butyl-6-hydrazino-N-methylpyridine-3-sulfonamide and 0.34 g of methyl 4-oxotetrahydrothiophene-3-carboxylate, 0.34 g of sodium 2-{5-[tert-butyl(methyl)-sulfamoyl]pyridin-2-yl}-2,6-dihydro-4H-thieno[3,4-c]pyrazol-3-olate is thus obtained in the form of a white lyophilizate.

Yield=67% m.p. (° C.)=130

M=C$_{15}$H$_{20}$N$_4$O$_3$S$_2$=368; M+H=369; Method 2: Tr=1.09 min.

$^1$H NMR, d6-DMSO, 400 MHz, δ (ppm): 8.6 (m, 2H); 8.0 (s, 1H); 3.75 (s, 2H); 3.6 (s, 2H); 2.9 (s, 3H); 1.3 (s, 9H).

Example 11

Sodium 2-[5-(Tert-butylcarbamoyl)Pyridin-2-yl]-2,6-dihydro-4H-thieno[3,4-c]Pyrazol-3-olate (Compound 33 of Table I)

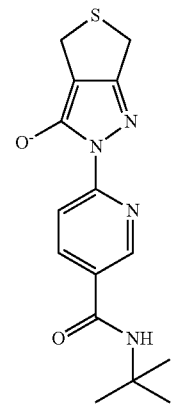 [SMILES: CC(C)(C)NC(=O)c1ccc(-n2nc3c(c2[O-])CSC3)nc1]

11.1. 6-(3-oxo-4,6-dihydro-1H-thieno[3,4-c]Pyrazol-2(3H)-yl)Pyridine-3-carboxylic Acid According to the process described in Example 1, starting with 1.75 g of 6-hydrazinopyridine-3-carboxylic acid and 1.8 g of methyl 4-oxotetrahydrothiophene-3-carboxylate, 2.5 g of 6-(3-oxo-4,6-dihydro-1H-thieno[3,4-c]pyrazol-2(3H)-yl) pyridine-3-carboxylic acid are obtained in the form of a yellow solid.

Yield=94%

$^1$H NMR, d6-DMSO, 400 MHz, δ (ppm): 12.5 (bs, 1H); 9.0 (s, 1H); 8.4 (d, 1H); 8.3 (bs, 1H); 4.1 (s, 2H); 3.8 (s, 2H).

11.2. Sodium 2-[5-(Tert-butylcarbamoyl)Pyridin-2-yl]-2,6-dihydro-4H-thieno[3,4-c]Pyrazol-3-olate To a mixture of 200 mg (0.84 mmol) of 6-(3-oxo-4,6-dihydro-1H-thieno[3,4-c]pyrazol-2(3H)-yl)pyridine-3-carboxylic acid, 90 µl (0.84 mmol) of tert-butylamine and 0.46 mL of DIEA in 3 mL of CH$_3$CN, cooled to 0° C., are added 365 mg of TBTU. The reaction medium is then allowed to warm slowly to room temperature, and stirring is continued for 12 hours. The reaction medium is concentrated under reduced pressure, and the residue obtained is taken up in 20 mL of water and extracted with DCM (3×20 mL), dried over Na$_2$SO$_4$, filtered and concentrated under reduced pressure, and purified on silica gel, eluting with a DCM/MeOH gradient of from 0 to 10% MeOH. 66 mg of the expected compound are obtained, and are taken up in 2 mL of a water/CH$_3$CN mixture (5:1) and 1 eq. of 1N NaOH, and then freeze-dried. 66 mg of sodium 2-[5-(tert-butylcarbamoyl)pyridin-2-yl]-2,6-dihydro-4H-thieno[3,4-c]pyrazol-3-olate are thus obtained in the form of a white lyophilizate.

Yield=25% m.p. (° C.)>260° C.

M=C$_{15}$H$_{17}$N$_4$O$_2$S=317; M+H=318; Method 2: Tr=0.94 min.

¹H NMR, d6-DMSO, 400 MHz, δ (ppm): 8.7 (s, 1H); 8.5 (d, 1H); 8.1 (d, 1H); 7.6 (s, 1H); 3.75 (s, 1H); 3.6 (s, 2H); 1.4 (s, 9H).

Example 12

Tert-butyl 6-(3-oxo-4,6-dihydro-1H-thieno[3,4-c]Pyrazol-2(3H)-yl)Pyridine-3-carboxylate (Compound 30 of Table I)

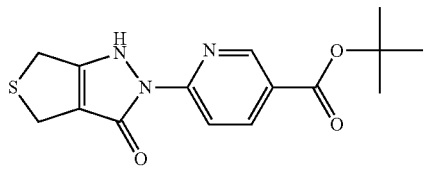 [SMILES: CC(C)(C)OC(=O)c1ccc(-n2[nH]c3c(c2=O)CSC3)nc1]

12.1. Tert-butyl 6-chloropyridine-3-carboxylate

To a suspension of 1 g (6.35 mmol) of 6-chloropyridine-3-carboxylic acid in 10 mL of refluxing toluene are added dropwise 7.6 mL (31.75 mmol) of 1,1-di-tert-butoxy-N,N-dimethylmethanamine, and the reaction medium is then refluxed for 30 minutes. After cooling to room temperature, the reaction medium is taken up in 200 mL of EtOAc, washed successively with water (2×100 mL), with saturated NaHCO₃ solution (100 mL) and brine (100 mL), dried over Na₂SO₄, filtered and concentrated under reduced pressure. 1.16 g of tert-butyl 6-chloropyridine-3-carboxylate are obtained in the form of a yellow oil, which is used without further purification in the following step.

Yield=86%

¹H NMR, d6-DMSO, 400 MHz, δ (ppm): 8.8 (s, 1H); 8.2 (d, 1H); 7.3 (d, 1H); 1.5 (s, 9H).

12.2. Tert-butyl 6-hydrazinopyridine-3-carboxylate

According to the process described in Example 4.2 starting with 1.16 g of tert-butyl 6-chloropyridine-3-carboxylate and 1 mL of hydrazine hydrate, 900 mg of tert-butyl 6-hydrazinopyridine-3-carboxylate are obtained in the form of a solid, which is used without further purification in the following step.

Yield=79%

¹H NMR, d6-DMSO, 400 MHz, δ (ppm): 8.7 (s, 1H); 8.0 (d, 1H); 6.6 (d, 1H); 6.3 (bs, 1H); 3.2 (bs, 2H); 1.5 (s, 9H).

12.3. Tert-butyl 6-(3-oxo-4,6-dihydro-1H-thieno[3,4-c]Pyrazol-2(3H)-yl)Pyridine-3-carboxylate According to the process described in Example 1, starting with 0.75 g of tert-butyl 6-hydrazinopyridine-3-carboxylate and 0.58 g of methyl 4-oxotetrahydrothiophene-3-carboxylate, 0.7 g of tert-butyl 6-(3-oxo-4,6-dihydro-1H-thieno[3,4-c]pyrazol-2(3H)-yl)pyridine-3-carboxylate is obtained in the form of a white solid.

Yield=61% m.p. (° C.)>250° C.

M=$C_{15}H_{17}N_3O_3S$=319; M+H=320; Method 2: Tr=1.27 min

¹H NMR, d6-DMSO, 400 MHz, δ (ppm): 8.9 (s, 1H); 8.4 (d, 1H); 8.2 (d, 1H); 4.0 (s, 2H); 3.7 (s, 2H), 3.4 (bs, 1H); 1.6 (s, 9H).

Example 13

Sodium 2-[5-(Propan-2-yl)Pyridin-2-yl]-2,6-dihydro-4H-thieno[3,4-c]Pyrazol-3-olate (Compound 44 of Table I)

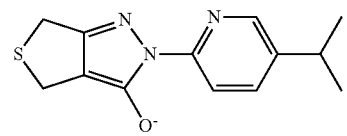 [SMILES: CC(C)c1ccc(-n2nc3c(c2[O-])CSC3)nc1]

13.1. 5-(Prop-1-en-2-yl)Pyridin-2-amine

A mixture of 2 g (11.56 mmol) of 5-bromopyridin-2-amine, 2.39 mL (13.87 mmol) of 4,4,5,5-tetramethyl-2-(prop-1-en-2-yl)-1,3,2-dioxaborolane and 3.83 g (27.74 mmol) of K₂CO₃ in 30 mL of DME and 10 mL of water is stirred for 5 minutes under argon, followed by addition of 1 g (2.1 mmol) of palladium bis(tri-t-butylphosphine). The reaction medium is heated for 3 hours at 80° C. After cooling to room temperature, the reaction medium is taken up in 40 mL of water and extracted with EtOAc (3×30 mL). The organic phases are washed with 0.5N HCl solution (3×30 mL). The aqueous phases are neutralized with 1N sodium hydroxide solution and then extracted with EtOAc (2×50 mL). The combined organic phases are dried over Na₂SO₄, filtered and concentrated under reduced pressure. 1.10 g of 5-(prop-1-en-2-yl)pyridin-2-amine are obtained in the form of a yellow solid, which is used without further purification in the following step.

Yield=71%

¹H NMR, CDCl₃, 400 MHz, δ (ppm): 8.0 (s, 1H); 7.6 (d, 1H); 6.5 (d, 1H); 5.3 (s, 1H); 5.0 (s, 1H); 4.5 (bs, 2H); 2.1 (s, 3H);

13.2. 5-(Propan-2-yl)Pyridin-2-amine

In a Parr flask, a mixture of 1.1 g (8.2 mmol) of 5-(prop-1-en-2-yl)pyridin-2-amine in 40 mL of MeOH and 0.11 g of 10% Pd/C is hydrogenated at 7 bar for 24 hours. The reaction mixture is then filtered through Whatman GF/F paper and concentrated under reduced pressure. 1.07 g of 5-(propan-2-yl)pyridin-2-amine are thus obtained in the form of a yellow oil, which is used without further purification in the following step.

Yield=96%.

¹H NMR, CDCl₃, 400 MHz, δ (ppm): 8.0 (s, 1H); 7.4 (dd, 1H); 6.5 (d, 1H); 4.4 (bs, 2H); 2.8 (m, 1H); 1.2 (s, 6H)

13.3. 2-hydrazinyl-5-(propan-2-yl)pyridine

According to the process described in Example 9.1, starting with 1.07 g of 5-(propan-2-yl)pyridin-2-amine, 0.52 g of 2-hydrazinyl-5-(propan-2-yl)pyridine is obtained in the form of a brown oil.

Yield=44%

13.4. sodium 2-[5-(propan-2-yl)pyridin-2-yl]-2,6-dihydro-4H-thieno[3,4-c]pyrazol-3-olate According to the process described in Example 8, starting with 520 mg of 2-hydrazinyl-5-(propan-2-yl)pyridine and 251 mg of methyl 4-oxotetrahydrothiophene-3-carboxylate, 102 mg of 2-[5-(propan-2-yl)pyridin-2-yl]-2,6-dihydro-4H-thieno[3,4-c]pyrazol-3-olate are obtained in the form of a lyophilizate.

Yield=11%
m.p. (° C.)>260° C.
M=C$_{13}$H$_{15}$N$_3$OS=261; M+H=262; Method 2: Tr=1.26 min
$^1$H NMR, d6-DMSO, 400 MHz, δ (ppm): 8.4 (d, 1H); 8.1 (s, 1H); 7.6 (dd, 1H); 3.7 (s, 2H); 3.6 (s, 2H); 2.9 (qt, 1H); 1.2 (s, 6H).

Example 14

Sodium 2-[4-(pyridin-3-ylmethoxy)pyridin-2-yl]-2,6-dihydro-4H-thieno[3,4-c]Pyrazol-3-olate (Compound 60 of Table II)

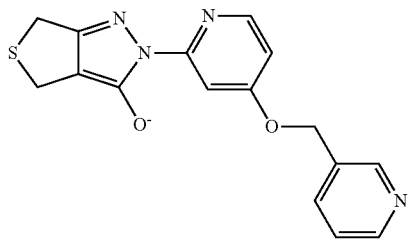 [SMILES: [O-]c1c2c(nn1-c1cc(OCc3cccnc3)ccn1)CSC2]

14.1. 2-chloro-4-(Pyridin-3-ylmethoxy)Pyridine

A mixture of 2 g (15.4 mmol) of 2-chloropyridin-4-ol, 3.82 g (15.1 mmol) of 3-(bromomethyl)pyridine hydrobromide, 3 g (75.6 mmol) of sodium hydroxide and 1.39 g (4.3 mmol) of tetrabutylammonium bromide in 90 mL of toluene is refluxed for 12 hours. After cooling to room temperature, the reaction medium is taken up in 300 mL of EtOAc, washed successively with water (2×100 mL), with saturated NaHCO$_3$ solution (100 mL) and with brine (100 mL), dried over Na$_2$SO$_4$, filtered, concentrated under reduced pressure and then purified by chromatography on silica gel, eluting with a 98/2 DCM/MeOH mixture. 2.5 g of 2-chloro-4-(pyridin-3-ylmethoxy)pyridine are obtained in the form of a yellow oil.

Yield=73%
$^1$H NMR, CDCl$_3$, 400 MHz, δ (ppm): 8.7 (s, 1H); 8.6 (d, 1H); 8.25 (d, 1H); 7.8 (d, 1H); 7.4 (dd, 1H); 7.0 (s, 1H); 6.8 (d, 1H); 5.1 (s, 2H)

14.2. 2-hydrazinyl-4-(Pyridin-3-ylmethoxy)Pyridine

A mixture of 0.5 g (2.27 mmol) of 2-chloro-4-(pyridin-3-ylmethoxy)pyridine and 2 mL (40.5 mmol) of hydrazine hydrate is heated at 80° C. for 12 hours. The reaction medium is then taken up in 30 mL of water and extracted with EtOAc (3×30 mL). The organic phases are combined, washed with brine (20 mL) and then dried over Na$_2$SO$_4$, filtered, concentrated under reduced pressure and purified on silica gel, eluting with a 95/5 DCM/MeOH mixture. 197 mg of 2-hydrazinyl-4-(pyridin-3-ylmethoxy)pyridine are obtained in the form of a yellow oil.

Yield=37%
$^1$H NMR, d6-DMSO, 400 MHz, δ (ppm): 8.7 (s, 1H); 8.5 (d, 1H); 7.9 (d, 1H); 7.8 (d, 1H); 7.4 (dd, 1H); 7.3 (s, 1H); 5.2 (s, 2H); 4.1 (s, 2H)

14.3. Sodium 2-[4-(Pyridin-3-ylmethoxy)Pyridin-2-yl]-2,6-dihydro-4H-thieno[3,4-c]Pyrazol-3-olate According to the process described in Example 8, starting with 197 mg of 2-hydrazinyl-4-(pyridin-3-ylmethoxy)pyridine and 146 mg of methyl 4-oxotetrahydrothiophene-3-carboxylate, 225 mg of sodium 2-(4-ethylpyridin-2-yl)-2,6-dihydro-4H-thieno[3,4-c]pyrazol-3-olate are obtained in the form of a white lyophilizate.

Yield=48%
m.p. (° C.)>260° C.
M=C$_{16}$H$_{14}$N$_4$O$_2$S=326; M+H=327; Method 2: Tr=0.71 min.
$^1$H NMR, d6-DMSO, 400 MHz, δ (ppm): 8.8 (s, 1H); 8.6 (d, 1H); 8.2 (s, 1H); 8.1 (d, 1H); 8.0 (d, 1H); 7.5 (t, 1H); 6.5 (d, 1H); 5.2 (s, 2H); 3.75 (s, 2H); 3.5 (s, 2H)

Example 15A

2-[5-(3-tert-butyl-1,2,4-oxadiazol-5-yl)Pyridin-2-yl]-1,2,4,6-tetrahydro-3H-thieno[3,4-c]Pyrazol-3-one (Compound 50A of Table I)

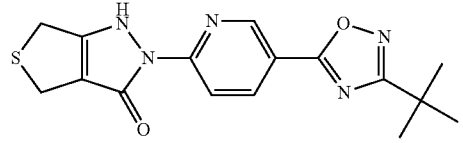 [SMILES: CC(C)(C)c1noc(-c2ccc(-n3[nH]c4c(c3=O)CSC4)nc2)n1]

15A.1. 5-(3-tert-butyl-1,2,4-oxadiazol-5-yl)-2-chloropyridine

To a solution of 3.8 g (21.5 mmol) of 6-chloropyridine-3-carbonyl chloride in 100 mL of toluene, in Dean-stark apparatus, are added portionwise 2.5 g (21.5 mmol) N-hydroxy-2,2-dimethylpropanimidamide, and the reaction medium is stirred for 2 hours at room temperature and then heated for 2 hours. After cooling to room temperature, the medium is concentrated under reduced pressure and purified by chromatography on silica gel, eluting with a cyclohexane/EtOAc gradient of from 0 to 10% EtOAc. 4.1 g of 5-(3-tert-butyl-1,2,4-oxadiazol-5-yl)-2-chloropyridine are obtained in the form of a white solid.

Yield=81%
$^1$H NMR, CDCl$_3$, 400 MHz, δ (ppm): 9.2 (s, 1H); 8.4 (dd, 1H); 7.5 (d, 1H); 7.8 (d, 1H); 1.4 (s, 9H)

15A.2. 5-(3-tert-butyl-1,2,4-oxadiazol-5-yl)-2-hydrazinylpyridine

According to the process described in Example 4.2 starting with 2 g of 5-(3-tert-butyl-1,2,4-oxadiazol-5-yl)-2-chloropyridine and 3.9 mL of hydrazine hydrate, 1.9 g of 5-(3-tert-butyl-1,2,4-oxadiazol-5-yl)-2-hydrazinylpyridine are obtained in the form of a solid, which is used without further purification in the following step.

Yield=97%
$^1$H NMR, d6-DMSO, 400 MHz, δ (ppm): 8.7 (s, 1H); 8.1 (d, 1H); 6.9 (d, 1H); 6.5 (bs, 1H); 3.5 (bs, 2H); 1.3 (s, 9H).

15A.3. 2-[5-(3-tert-butyl-1,2,4-oxadiazol-5-yl)Pyridin-2-yl]-1,2,4,6-tetrahydro-3H-thieno[3,4-c]Pyrazol-3-one According to the process described in Example 1, starting with 0.6 g of 5-(3-tert-butyl-1,2,4-oxadiazol-5-yl)-2-hydrazinylpyridine and 0.41 g of methyl 4-oxotetrahydrothiophene-3-carboxylate, 0.32 g of 2-[5-(3-tert-butyl-1,2,4-oxadiazol-5-yl)pyridin-2-yl]-1,2,4,6-tetrahydro-3H-thieno[3,4-c]pyrazol-3-one is obtained in the form of a white solid.

Yield=38% m.p. (° C.)=240° C.

M=$C_{16}H_{17}N_5O_2S$=343; M+H=344; Method 2: Tr=1.34 min.

$^1$H NMR, d6-DMSO, 400 MHz, δ (ppm): 12.3 (bs, 1H); 9.1 (s, 1H); 8.6 (d, 1H); 8.4 (d, 1H); 4.0 (s, 2H); 3.8 (s, 2H); 1.4 (s, 9H).

Example 15B

2-[5-(5-tert-butyl-1,2,4-oxadiazol-3-yl)Pyridin-2-yl]-1,2,4,6-tetrahydro-3H-thieno[3,4-c]Pyrazol-3-one (Compound 50B of Table I)

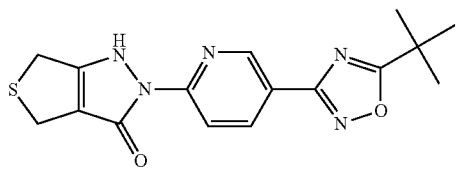 [SMILES: CC(C)(C)c1nc(-c2ccc(-n3[nH]c4c(c3=O)CSC4)nc2)no1]

15B.1 5-(5-tert-butyl-1,2,4-oxadiazol-3-yl)-2-chloropyridine

A mixture of 1.5 g (8.74 mmol) of 6-chloro-N'-hydroxypyridine-3-carboximidamide and 1.13 mL (9.18 mmol) of trimethylacetyl chloride in 15 mL of toluene is stirred for 1 hour at room temperature and then refluxed for 4 hours. The medium is filtered. The insoluble material formed is dissolved in 15 mL of AcOH and then heated at 60° C. for 5 hours. After cooling to room temperature, the medium is concentrated under reduced pressure and then purified by chromatography on silica gel, eluting with a cyclohexane/EtOAc mixture (9/1). 0.39 g of 5-(5-tert-butyl-1,2,4-oxadiazol-3-yl)-2-chloropyridine is obtained in the form of a white solid.

Yield=21%

15.B2 2-[5-(5-tert-butyl-1,2,4-oxadiazol-3-yl)Pyridin-2-yl]-1,2,4,6-tetrahydro-3H-thieno[3,4-c]Pyrazol-3-one (Compound 50 B of Table I)

The compound is obtained, according to Processes 15.A2-15.A3, starting with 5-(5-tert-butyl-1,2,4-oxadiazol-3-yl)-2-chloropyridine and methyl 4-oxotetrahydrothiophene-3-carboxylate, in the form of a white solid.

m.p. (° C.)=240° C.

M=$C_{16}H_{17}N_5O_2S$=343; M+H=344; Method 2: Tr=1.39 min.

$^1$H NMR, d6-DMSO, 400 MHz, δ (ppm): 12.3 (bs, 1H); 9.1 (s, 1H); 8.5 (d, 1H); 8.4 (d, 1H); 4.1 (s, 2H); 3.8 (s, 2H); 1.5 (s, 9H)

Example 16

N-cyclopentyl-N-(2,3-dihydroxypropyl)-6-(3-oxo-4,6-dihydro-1H-thieno[3,4-c]Pyrazol-2(3H)-yl)pyridine-3-sulfonamide (Compound 53 of Table I)

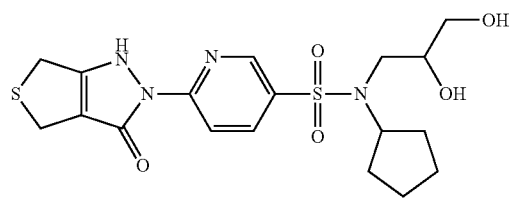 [SMILES: O=c1c2c([nH]n1-c1ccc(S(=O)(=O)N(CC(O)CO)C3CCCC3)cn1)CSC2]

16.1. 6-chloro-N-cyclopentylpyridine-3-sulfonamide

According to Process 4.1, starting with 5 g of 6-chloropyridine-3-sulfonyl chloride and 2 g of cyclopentylamine, 5.1 g 6-chloro-N-cyclopentylpyridine-3-sulfonamide are obtained in the form of a yellow solid.

Yield=83%

$^1$H NMR, CDCl$_3$, 400 MHz, δ (ppm): 8.9 (s, 1H); 8.0 (d, 1H); 7.4 (d, 1H); 4.5 (d, 1H); 3.6 (q, 1H); 1.8-1.2 (m, 8H)

16.2 6-chloro-N-cyclopentyl-N-(Prop-2-en-1-yl)Pyridine-3-sulfonamide

According to Process 10.2, starting with 1 g of 6-chloro-N-cyclopentylpyridine-3-sulfonamide and 0.42 mL of allyl bromide, 1.2 g of 6-chloro-N-phenyl-N-(prop-2-en-1-yl)pyridine-3-sulfonamide are obtained in the form of an orange-coloured oil.

Yield=94%

$^1$H NMR, CDCl$_3$, 400 MHz, δ (ppm): 8.9 (s, 1H); 8.0 (d, 1H); 7.4 (d, 1H); 5.7 (dd, 1H); 5.2 (dd, 1H); 5.1 (d, 1H); 4.2 (m, 1H); 3.7 (d, 2H); 1.8-1.2 (m, 8H)

16.3. 6-chloro-N-cyclopentyl-N-(2,3-dihydroxypropyl)Pyridine-3-sulfonamide

To a solution of 1.1 g (3.7 mmol) of 6-chloro-N-cyclopentyl-N-(prop-2-en-1-yl)pyridine-3-sulfonamide in 15 mL of a mixture (1/1) of tBuOH and water are added, at room temperature, 1.2 g (10.3 mmol) of NMO and 0.52 mL (0.04 mmol) of 2.5% OsO$_4$ in tBuOH. Stirring is continued for 12 hours. The medium is then diluted with 200 mL of water and extracted with Et$_2$O (2×100 mL), dried over Na$_2$SO$_4$, filtered and concentrated under reduced pressure. 0.92 g of 6-chloro-N-cyclopentyl-N-(2,3-dihydroxypropyl)pyridine-3-sulfonamide is obtained in the form of a brown solid, which is used without further purification in the following step.

Yield=75%.

$^1$H NMR, CDCl$_3$, 400 MHz, δ (ppm): 8.8 (s, 1H); 8.1 (d, 1H); 7.5 (d, 1H); 4.3 (m, 1H); 4.0 (m, 1H); 3.6 (dd, 2H); 3.2 (dd, 2H); 1.8-1.4 (m, 10H)

16.4. 6-chloro-N-cyclopentyl-N-[(2,2-dimethyl-1,3-dioxolan-4-yl)methyl]Pyridine-3-sulfonamide A mixture of 0.83 g (2.48 mmol) of 6-chloro-N-cyclopentyl-N-(2,3-dihydroxypropyl)pyridine-3-sulfonamide, 0.67 mL (5.45 mmol) of 2,2-dimethoxypropane and 47 mg of pTsOH in 5 mL of DMF is stirred for 3 hours at room temperature. The medium is taken up in 100 mL of EtOAc, washed with 50 mL of saturated NaHCO₃ solution and 50 mL of water, and then dried over Na₂SO₄, filtered and concentrated under reduced pressure. 0.92 g 6-chloro-N-cyclopentyl-N-[(2,2-dimethyl-1,3-dioxolan-4-yl)methyl]pyridine-3-sulfonamide is obtained in the form of a brown oil, which is used without further purification in the following step.

Yield=98%.

¹H NMR, CDCl₃, 400 MHz, δ (ppm): 8.8 (s, 1H); 8.0 (d, 1H); 7.3 (d, 1H); 4.3 (m, 1H); 4.0 (m, 2H); 3.7 (m, 1H), 3.3 (dd, 1H); 3.1 (dd, 1H); 1.8-1.3 (m, 8H); 1.3 (s, 3H); 1.2 (s, 3H)

16.5. N-cyclopentyl-N-[(2,2-dimethyl-1,3-dioxolan-4-yl)Methyl]-6-hydrazinylpyridine-3-sulfonamide According to Process 4.2, starting with 0.92 g of 6-chloro-N-cyclopentyl-N-[(2,2-dimethyl-1,3-dioxolan-4-yl)methyl] pyridine-3-sulfonamide and 0.24 mL of hydrazine hydrate, 0.85 g of N-cyclopentyl-N-[(2,2-dimethyl-1,3-dioxolan-4-yl)methyl]-6-hydrazinylpyridine-3-sulfonamide is obtained in the form of a yellow oil.

Yield=99%

16.6. N-cyclopentyl-N-[(2,2-dimethyl-1,3-dioxolan-4-yl)Methyl]-6-(3-oxo-4,6-dihydro-1H-thieno[3,4-c]Pyrazol-2(3H)-yl)Pyridine-3-sulfonamide According to Process 1, starting with 0.4 g of N-cyclopentyl-N-[(2,2-dimethyl-1,3-dioxolan-4-yl)methyl]-6-hydrazinylpyridine-3-sulfonamide and 0.173 g of methyl 4-oxotetrahydrothiophene-3-carboxylate, 470 mg N-cyclopentyl-N-[(2,2-dimethyl-1,3-dioxolan-4-yl)methyl]-6-(3-oxo-4,6-dihydro-1H-thieno[3,4-c]pyrazol-2(3H)-yl)pyridine-3-sulfonamide are obtained in the form of a brown solid.

Yield=97%

16.7. N-cyclopentyl-N-(2,3-dihydroxypropyl)-6-(3-oxo-4,6-dihydro-1H-thieno[3,4-c]Pyrazol-2(3H)-yl)Pyridine-3-sulfonamide A solution of 470 mg (0.54 mmol) of 6 N-cyclopentyl-N-[(2,2-dimethyl-1,3-dioxolan-4-yl)methyl]-6-(3-oxo-4,6-dihydro-1H-thieno[3,4-c]pyrazol-2(3H)-yl)pyridine-3-sulfonamide in 1 mL of AcOH is heated at 80° C. for 4 hours. The medium is concentrated under reduced pressure and then purified by reverse-phase chromatography on a C18 column, eluting with a 10⁻³ N HCl/CH₃CN gradient of from 0 to 100% CH₃CN. 48 mg of N-cyclopentyl-N-(2,3-dihydroxypropyl)-6-(3-oxo-4,6-dihydro-1H-thieno[3,4-c]pyrazol-2(3H)-yl) pyridine-3-sulfonamide are obtained in the form of a white solid.

Yield=30% m.p. (° C.)=190

M=C₁₈H₂₄N₄O₅S₂=440; M+H=441; Method 2: Tr=0.89 min.

¹H NMR, d6-DMSO, 400 MHz, δ (ppm): 12.1 (bs, 1H); 8.7 (s, 1H); 8.3 (bs, 1H); 8.2 (d, 1H); 4.7 (s, 1H); 4.5 (t, 1H); 4.1 (m, 1H); 3.9 (s, 2H); 3.6 (m, 3H); 3.4-3.2 (m, 3H); 2.8 (dd, 1H); 1.7-1.2 (m, 8H)

Example 17

2,2-dimethylpropyl 6-[5-(Methylsulfonyl)-3-oxo-1,3,4,5,6,7-hexahydro-2H-pyrazolo[4,3-c]Pyridin-2-yl] Pyridine-3-carboxylate (Compound 54 of Table I)

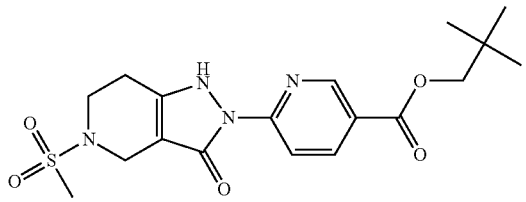 [SMILES: CC(C)(C)COC(=O)c1ccc(-n2[nH]c3c(c2=O)CN(S(C)(=O)=O)CC3)nc1]

17.1. Methyl 1-(methylsulfonyl)-4-oxopiperidine-3-carboxylate

To a mixture of 1 g (6.36 mmol) of methyl 4-oxopiperidine-3-carboxylate hydrochloride and 2.2 mL of Et₃N in 12 mL of DCM is added dropwise at room temperature 0.5 mL of mesyl chloride. The reaction medium is stirred for 1 hour and then taken up in 50 mL of EtOAc, washed with 20 mL of water and 20 mL of brine and then dried over Na₂SO₄, filtered and concentrated under reduced pressure. 0.35 g of methyl 1-(methylsulfonyl)-4-oxopiperidine-3-carboxylate is obtained.

Yield=23%

17.2. 2,2-dimethylpropyl 6-chloropyridine-3-carboxylate

To a solution of 10 g (56.8 mmol) of 6-chloropyridine-3-carbonyl chloride in 100 mL of anhydrous toluene are added under argon, at room temperature, 15 g (170.4 mmol) of 2,2-dimethylpropanol. The reaction medium is then heated at 80° C. for 6 hours. After cooling to room temperature, the medium is concentrated and the residue obtained is taken up in 800 mL of EtOAc, washed successively with water (2×200 mL), with saturated NaHCO₃ solution (2×200 mL) and with brine (100 mL), dried over Na₂SO₄, then concentrated under reduced pressure and purified by chromatography on a column of silica gel, eluting with a cyclohexane/EtOAc gradient of from 0 to 5% EtOAc. 11.9 g of 2,2-dimethylpropyl 6-chloropyridine-3-carboxylate are obtained in the form of a white powder.

Yield=92%.

¹H NMR, CDCl₃, 400 MHz, δ (ppm): 7.5 (m, 5H); 4.2 (m, 5H); 3.0 (dd, 2H, 1.0 (t, 6H)

17.3. 2,2-dimethylpropyl 6-hydrazinylpyridine-3-carboxylate

According to the process described in Example 4.2, starting with 11.9 g (52.26 mmol) of 2,2-dimethylpropyl 6-chloropyridine-3-carboxylate, 4.3 g of 2,2-dimethylpropyl 6-hydrazinylpyridine-3-carboxylate are obtained in the form of a white powder.

Yield=37%

¹H NMR, d6-DMSO, 400 MHz, δ (ppm): 8.7 (s, 1H); 8.15 (d, 1H); 6.9 (d, 1H); 4.0 (s, 2H); 3.5 (bs, 1H); 1.0 (s, 9H).

17.4. 2,2-dimethylpropyl 6-[5-(methylsulfonyl)-3-oxo-1,3,4,5,6,7-hexahydro-2H-pyrazolo[4,3-c]pyridin-2-yl]pyridine-3-carboxylate According to Process 1, starting with 0.21 g of methyl 1-(methylsulfonyl)-4-oxopiperidine-3-carboxylate and 0.2 g of 2,2-dimethylpropyl 6-hydrazinylpyridine-3-carboxylate, 10 mg of 2,2-dimethylpropyl 6-[5-(methylsulfonyl)-3-oxo-1,3,4,5,6,7-hexahydro-2H-pyrazolo[4,3-c]pyridin-2-yl]pyridine-3-carboxylate are obtained.

Yield=3% m.p. (° C.)=230

$M=C_{18}H_{24}N_4O_5S=408$; M+H=409; Method 2: Tr=1.11 min.

¹H NMR, d6-DMSO, 400 MHz, δ (ppm): 12.2 (bs, 1H); 9.0 (s, 1H); 8.6 (bs, 1H); 8.5 (d, 1H); 4.1 (s, 2H); 4.0 (s, 2H); 3.5 (t, 2H); 3.0 (s, 3H); 2.8 (t, 2H); 1.0 (s, 9H).

The tables that follow illustrate the chemical structures and the physical properties of a few examples of compounds according to the invention.

Table I illustrates compounds of formula (I) according to the invention in which R2 is in the beta position. These compounds are referred to hereinbelow as compounds of formula (I').

Table II illustrates compounds of formula (I) according to the invention in which R2 is in the gamma position. These compounds are referred to hereinbelow as compounds of formula (I").

Tables I and II below illustrate the chemical structures and the physical properties of a few examples of compounds according to the invention.

In these tables:

- in the "salt" column, "-" represents a compound in free base form, whereas "CF₃COOH", "HCl" and "Na" represent, respectively, a compound in the form of the trifluoroacetic acid salt, in the form of the hydrochloride salt and in the form of the sodium salt;
- in the other columns, "-" means that the substituent under consideration is not present on the molecule;
- Me, Et, n-Pr, i-Pr, n-Bu and i-Bu represent, respectively, the methyl, ethyl, n-propyl, isopropyl, n-butyl and isobutyl groups;
- Ph and Bn represent, respectively, the phenyl and benzyl groups;
- the "m.p." column indicates the melting point, in ° C., of the compound under consideration;
- the peak MH⁺ identified by mass spectrometry, and the high-performance liquid chromatography analytical methods used and detailed previously, are indicated, respectively, in the "LC/MS" column and the "Method" column.

TABLE I

| No. | X | n | m | o | R1 | Structure |
|-----|------|---|---|---|----|-----------|
| 1 | S | 1 | 1 | 0 | — | (thiophene-fused pyrazolone) |
| 2 | CH₂ | 2 | 1 | 0 | — | (cyclohexane-fused pyrazolone) |
| 3 | —CH(Me)— | 1 | 2 | 0 | — | (methyl-substituted cyclohexane-fused pyrazolone) |
| 4 | CH₂ | 3 | 1 | 0 | — | (cycloheptane-fused pyrazolone) |

TABLE I-continued

| | | | | | | |
|---|---|---|---|---|---|---|
| 5 | benzylamine-N | 2 | 1 | 0 | — | benzyl-piperidine-pyrazolone |
| 6 | CH₂ | 2 | 1 | 0 | — | tetrahydroindazolone |
| 7 | CH₂ | 1 | 1 | 0 | — | cyclopenta-pyrazolone |
| 8 | N-benzyl | 2 | 1 | 0 | — | benzyl-piperidine-pyrazolone |
| 9 | S | 1 | 1 | 0 | — | thieno-pyrazolone |
| 10 | N-benzyl | 2 | 1 | 0 | — | benzyl-piperidine-pyrazolone |
| 11 | —CH(OMe)— | 0 | 2 | 0 | — | methoxy-cyclopenta-pyrazolone |
| 12 | S | 2 | 1 | 0 | — | thiopyrano-pyrazolone |
| 13 | S | 2 | 1 | 0 | — | thiopyrano-pyrazolone |

TABLE I-continued

| | | | | | | |
|---|---|---|---|---|---|---|
| 14 | S | 1 | 1 | 0 | — | (thienopyrazolone structure) |
| 15 | S | 1 | 1 | 0 | — | (thienopyrazolone structure) |
| 16 | S | 1 | 1 | 0 | — | (thienopyrazolone structure) |
| 17 | S | 1 | 1 | 0 | — | (thienopyrazolone structure) |
| 18 | S | 1 | 1 | 0 | — | (thienopyrazolone structure) |
| 19 | S | 1 | 1 | 0 | — | (thienopyrazolone structure) |
| 20 | S | 1 | 1 | 0 | — | (thienopyrazolone structure) |
| 21 | S | 1 | 1 | 0 | — | (thienopyrazolone structure) |
| 22 | S | 1 | 1 | 0 | — | (thienopyrazolone structure) |
| 23 | S | 1 | 1 | 0 | — | (thienopyrazolone structure) |

TABLE I-continued
| | | | | | | |
|---|---|---|---|---|---|---|
| 24 | S | 3 | 0 | 0 | — | 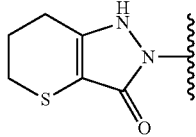 [SMILES: *n1[nH]c2c(c1=O)CCCC2] |
| 25 | O | 2 | 1 | 0 | — | 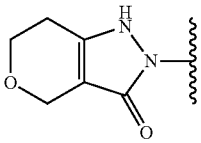 [SMILES: *n1[nH]c2c(c1=O)COCC2] |
| 26 | S | 1 | 1 | 0 | — | 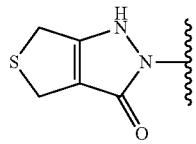 [SMILES: *n1[nH]c2c(c1=O)CSC2] |
| 27 | S | 1 | 1 | 0 | — | 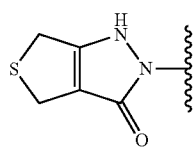 [SMILES: *n1[nH]c2c(c1=O)CSC2] |
| 28 |  OtBu | 2 | 1 | 0 | — | 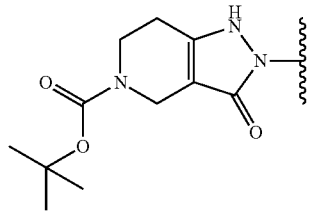 [SMILES: *n1[nH]c2c(c1=O)CN(C(=O)OC(C)(C)C)CC2] |
| 29 |  Me | 2 | 1 | 0 | — | 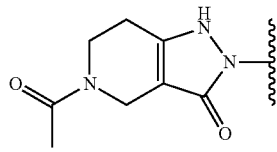 [SMILES: *n1[nH]c2c(c1=O)CN(C(C)=O)CC2] |
| 30 | S | 1 | 1 | 0 | — | 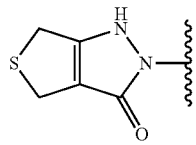 [SMILES: *n1[nH]c2c(c1=O)CSC2] |
| 31 | S | 1 | 1 | 0 | — | 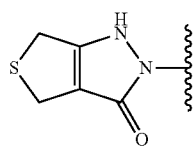 [SMILES: *n1[nH]c2c(c1=O)CSC2] |
| 32 | S | 1 | 1 | 0 | — | 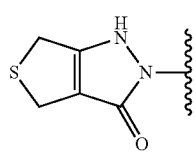 [SMILES: *n1[nH]c2c(c1=O)CSC2] |
| 33 | S | 1 | 1 | 0 | — | 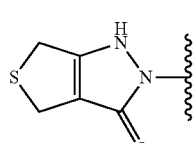 |

TABLE I-continued

| | | | | | | |
|---|---|---|---|---|---|---|
| 34 | S | 1 | 1 | 0 | — | (thieno-pyrazolone structure) |
| 35 | N-CH2-Ph | 3 | 0 | 1 | Oxo | (benzyl-pyrazolo-pyridinedione structure) |
| 36 | S | 1 | 1 | 0 | — | (thieno-pyrazolone structure) |
| 37 | —CH2— | 4 | 1 | 0 | — | (cycloheptano-pyrazolone structure) |
| 38 | S | 1 | 1 | 0 | — | (thieno-pyrazolone structure) |
| 40 | S | 1 | 1 | 0 | — | (thieno-pyrazolone structure) |
| 41 | S | 1 | 1 | 0 | — | (thieno-pyrazolone structure) |
| 42 | S | 1 | 1 | 0 | — | (thieno-pyrazolone structure) |
| 43 | S | 1 | 1 | 0 | — | (thieno-pyrazolone structure) |
| 44 | S | 1 | 1 | 0 | — | (thieno-pyrazolone structure) |

TABLE I-continued
| | | | | | | |
|---|---|---|---|---|---|---|
| 45 | S | 1 | 1 | 1 | —COOMe | 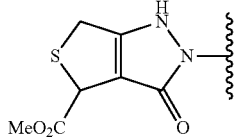 [SMILES: *n1[nH]c2c(c1=O)C(C(=O)OC)SC2] |
| 46 | S | 1 | 1 | 0 | — | 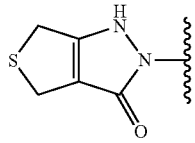 [SMILES: *n1[nH]c2c(c1=O)CSC2] |
| 47 | —CH(OMe)— | 0 | 2 | 0 | — | 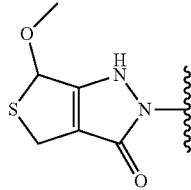 [SMILES: *n1[nH]c2c(c1=O)CSC2OC] |
| 48 | CH$_2$ | 1 | 1 | 0 | — | 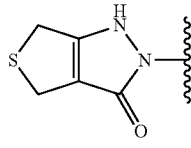 [SMILES: *n1[nH]c2c(c1=O)CSC2] |
| 49 | S | 1 | 1 | 0 | — | 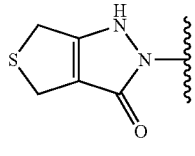 [SMILES: *n1[nH]c2c(c1=O)CSC2] |
| 50A | S | 1 | 1 | 0 | | 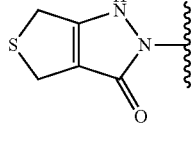 |
| 50B | S | 1 | 1 | 0 | — | 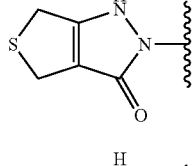 |
| 51 | S | 1 | 1 | 0 | — | 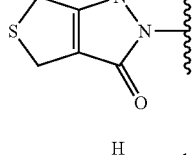 |
| 52 | —CH$_2$— | 1 | 1 | 0 | — | 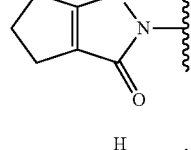 |
| 53 | S | 1 | 1 | 0 | — | 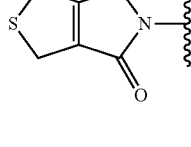 |

TABLE I-continued

| No. | | | | | | |
|---|---|---|---|---|---|---|
| 54 | (MeSO2)N- structure | 2 | 1 | 0 | — | 5-methylsulfonyl-tetrahydropyrazolo[4,3-c]pyridin-3-one |
| 55 | —CH2— | 2 | 1 | 0 | — | 4,5,6,7-tetrahydro-2H-indazol-3-one |
| 56 | BnN- structure | 2 | 1 | 0 | — | 5-benzyl-tetrahydropyrazolo[4,3-c]pyridin-3-one |
| 57 | —CH(Me)— | 1 | 2 | 0 | — | 6-methyl-4,5,6,7-tetrahydro-2H-indazol-3-one |
| 58 | MeO(C=O)N- structure | 2 | 1 | 0 | — | 5-methoxycarbonyl-tetrahydropyrazolo[4,3-c]pyridin-3-one |

| No. | R2 | m.p. | LC-MS (M + H) | Salt | Method |
|---|---|---|---|---|---|
| 1 | H | 152 | 220 | — | 2 |
| 2 | methylsulfonyl-piperidine | 206 | 363 | — | 1 |
| 3 | methylsulfonyl-piperidine | 240 | 377 | — | 1 |
| 4 | methylsulfonyl-piperidine | 240 | 391 | — | 1 |
| 5 | N-ethyl-N-phenyl-methanesulfonamide | 210 | 490 | CF3CO2H | 1 |

TABLE I-continued

| | | | | | |
|---|---|---|---|---|---|
| 6 | ![structure: methylsulfonyl-3,5-dimethylpiperidine] | 230 | 391 | — | 1 |
| 7 | H | 156 | 202 | — | 2 |
| 8 | ![structure: N,N-diethyl methanesulfonamide] | 248 | 442 | — | 2 |
| 9 | ![structure: N-ethyl-N-phenyl methanesulfonamide] | 208 | 403 | — | 2 |
| 10 | ![structure: N,N-diisopropyl methanesulfonamide] | 160 | 470 | — | 2 |
| 11 | H | 76 | 232 | — | 2 |
| 12 | H | 175 | 234 | — | 2 |
| 13 | ![structure: N-ethyl-N-phenyl methanesulfonamide] | 176 | 417 | — | 2 |
| 14 | ![structure: N,N-dimethyl methanesulfonamide] | 327 | >260 | — | 2 |
| 15 | ![structure: methylsulfonyl pyrrolidine] | 152 | 353 | — | 2 |
| 16 | ![structure: N-cyclopropyl methanesulfonamide] | 262 | 339 | — | 2 |
| 17 | ![structure: N-isopropyl methanesulfonamide] | 258 | 341 | — | 2 |
| 18 | ![structure: N-tert-butyl methanesulfonamide] | 257 | 355 | — | 2 |

TABLE I-continued
| | | | | | |
|---|---|---|---|---|---|
| 19 | 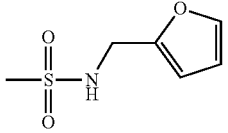 | 238 | 379 | — | 2 |
| 20 | 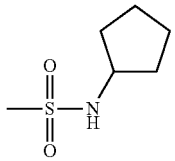 | >260 | 367 | — | 2 |
| 21 | 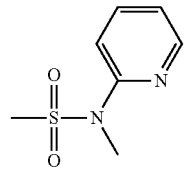 | 226 | 390 | — | 2 |
| 22 | 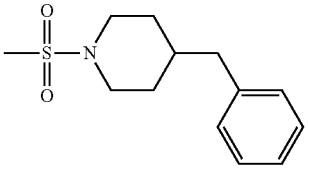 | 254 | 457 | — | 2 |
| 23 | 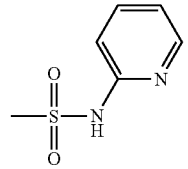 | >260 | 376 | — | 2 |
| 24 | 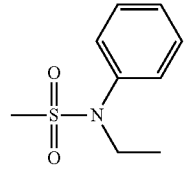 | 198 | 417 | — | 2 |
| 25 | 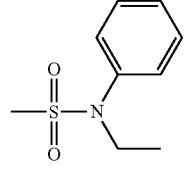 | 164 | 401 | — | 2 |
| 26 | 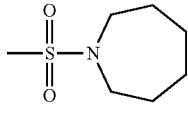 | 236 | 381 | — | 2 |
| 27 | 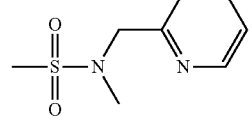 | 198 | 404 | HCl | 2 |

TABLE I-continued

| # | Structure | | | | |
|---|---|---|---|---|---|
| 28 | PhN(Et)SO₂Me | 192 | 500 | — | 2 |
| 29 | PhN(Et)SO₂Me | 118 | 442 | — | 2 |
| 30 | —CO₂—tBu | >250 | 320 | — | 2 |
| 31 | Me | >220 | 234 | Na | 2 |
| 32 | MeSO₂N(Et)tBu | >260 | 383 | Na | 2 |
| 33 | MeC(O)NH—tBu | >260 | 318 | Na | 2 |
| 34 | —OMe | >220 | 250 | Na | 2 |
| 35 | PhN(Et)SO₂Me | >250 | 504 | Na | 2 |
| 36 | MeSO₂N(Me)tBu | 130 | 369 | Na | 2 |
| 37 | PhN(Et)SO₂Me | 200 | 427 | — | 1 |
| 38 | MeSO₂N(Et)Et | 192 | 355 | — | 2 |
| 40 | (3-pyridyl)N(Me)SO₂Me | 182 | 390 | HCl | 2 |

TABLE I-continued

| # | Structure | Col3 | Col4 | Col5 | Col6 |
|---|---|---|---|---|---|
| 41 | methanesulfonyl-N-cyclopentyl-N-ethyl | >260 | 395 | Na | 2 |
| 42 | cyclopentyl acetate | 244 | 332 | — | 2 |
| 43 | isobutyl acetate | 200 | 320 | — | 2 |
| 44 | isobutyl | >260 | 262 | Na | 2 |
| 45 | N-phenyl-N-ethyl methanesulfonamide | 158 | 461 | — | 2 |
| 46 | isopropyl acetate | 220 | 306 | — | 2 |
| 47 | N-phenyl-N-ethyl methanesulfonamide | 220 | 414 | Na | 2 |
| 48 | N-phenyl-N-ethyl methanesulfonamide | 204 | 385 | — | 2 |
| 49 | neopentyl acetate | 204 | 334 | — | 2 |
| 50A | 5-methyl-3-tert-butyl-1,2,4-oxadiazole | 240 | 344 | | 2 |

TABLE I-continued

| | | | | | |
|---|---|---|---|---|---|
| 50B | 3-methyl-5-tert-butyl-1,2,4-oxadiazole | 240 | 344 | — | 2 |
| 51 | N-cyclopentyl-N-methyl methanesulfonamide | 208 | 381 | — | 2 |
| 52 | N-cyclopentyl-N-ethyl methanesulfonamide | 220 | 377 | — | 2 |
| 53 | N-cyclopentyl-N-(2,3-dihydroxypropyl) methanesulfonamide | 190 | 441 | — | 2 |
| 54 | neopentyl acetate | 230 | 409 | — | 2 |
| 55 | N-phenyl-N-ethyl methanesulfonamide | 200 | 399 | — | 1 |
| 56 | rac 3,5-dimethyl-1-(methanesulfonyl)piperidine | 220 | 482 | — | 1 |
| 57 | rac 3,5-dimethyl-1-(methanesulfonyl)piperidine | 215 | 405 | — | 1 |
| 58 | N-phenyl-N-ethyl methanesulfonamide | 86 | 458 | — | 2 |

TABLE II (I″)

| No. | X | n | m | o | R1 | | R2 | R2' | m.p. | LC-MS(M + H) | Salt | Method |
|---|---|---|---|---|---|---|---|---|---|---|---|---|
| 59 | S | 1 | 1 | 0 | — | thieno-pyrazolone | —OMe | — | 254 | 250 | — | 2 |
| 60 | S | 1 | 1 | 0 | — | thieno-pyrazolone | —NMe₂ | — | 182 | 263 | HCl | 2 |
| 61 | S | 1 | 1 | 0 | — | thieno-pyrazolone | Et— | — | >260 | 247 | Na | 2 |
| 62 | S | 1 | 1 | 0 | — | thieno-pyrazolone | Me | — | >250 | 234 | Na | 2 |
| 63 | S | 1 | 1 | 0 | — | thieno-pyrazolone | —OCH₂Ph | — | >250 | 326 | Na | 2 |
| 64 | S | 1 | 1 | 0 | — | thieno-pyrazolone | pyridin-3-yl-methoxy | — | >260 | 327 | Na | 2 |
| 65 | S | 1 | 1 | 0 | — | thieno-pyrazolone | isopropyl | — | 92 | 262 | — | 2 |

The compounds according to the invention underwent pharmacological trials in order to determine their properties, with, in particular:
- an in vitro test of direct measurement of stabilization of the protein HIF1-alpha, a transcription factor constitutively expressed in cells but degraded under normal oxygen conditions by the ubiquitin/proteasome system;
- a functional test for measuring in He3pB cells the secretion of VEGF and EPO, which are two markers of activation of HIF1-alpha in hepatocytes.

These two tests are described below.

1. Measurement of the Stabilization of HIF1-Alpha in HEKEA Cells 1.1 Object

HIF is a transcription factor involved in the adaptation of cells to hypoxia. This transcription factor is at the minimum a heterodimer formed from two proteins, ARNT and HIF1-alpha. ARNT is constitutively and stably expressed in cells and the main part of the transcription complex regulation is performed via stabilization of the protein HIF1-alpha. In point of fact, this protein, under normal oxygen conditions (20%, approximately equivalent to the value of ambient oxygen), is hydroxylated specifically on two prolines (proline 402 and 564 for the human protein) via HIF prolyl-hydroxylases, resulting in the binding of the von Hippell Lindau (VHL) protein. This binding of VHL to HIF1-alpha then causes the degradation of HIF1-alpha via the ubiquitin/proteasome system. Under hypoxia ($O_2$<5% in the cell tests), the HIF prolyl-hydroxylases are inhibited, which is reflected by an increase in the amount of HIF1-alpha protein in the cells. This protein can then combine with ARNT to transfer into the nucleus and activate its target genes.

Since the genes activated by HIF are involved in the adaptive response of cells to hypoxia and of tissues to ischaemia, the object is to identify and characterize compounds that stabilize HIF1-alpha in cells in order to amplify or mimic its beneficial effect.

Many tests exist describing the indirect measurement of the activity of HIF via reporter gene systems (HRE-luciferase) or via the measurement of HIF-induced proteins (for example VEGF or EPO). Furthermore, the only tests that allow direct measurement of the amount of HIF1-alpha protein in cells are tests using antibodies, for instance Western blotting comprising phases of cell extraction (total lysates or nuclear extracts) that are consuming in terms of cells and time, thus limiting the compound screening capacity. The object was thus to develop a sensitive screening test, adaptable to 384-well plates, for directly measuring the amount of HIF1-alpha protein in the nucleus of cells. This test was established in HEK cells (human epithelial cells derived from a renal adenocarcinoma).

1.2 Test Principle

The test is a cell test based on the principle of enzyme complementation, the enzyme used herein being beta-galactosidase. HEKEA cells are HEK cells stably expressing, and restricted in their nucleus, mutant beta-galactosidase (omega fragment, also known as EA) (line sold by DiscoverX). This construct makes it possible to obtain beta-galactosidase activity only when the protein comprising the Prolabel complementation fragment has migrated into the nucleus.

The protein of interest comprising the Prolabel fragment is in this case an HIF1-alpha or HIF1-alpha mutated at the two prolines 402 and 564 replaced with alanines, is C-terminal fused via molecular biology (DiscoverX vector sold by Clontech) with the small complementation peptide fragment (Prolabel or ED, about 4 kDa). The vector coding for the chimeric protein HIF1-alpha_Prolabel is then transfected into HEKEA cells to obtain stable clones (HEKEA_HIF1-alphaPLBL).

The amount of C-terminal Prolabel-"labelled" HIF1-alpha protein obtained after treating the cells to hypoxia or compounds that are potentially HIF activators is measured by adding to the cells a lysis buffer containing a chemiluminescent substrate for beta-galactosidase.

The measurement of the beta-galactosidase activity will be proportional to the amount of Prolabel and thus of HIF1-alpha that has migrated into the nucleus of the cells.

Experiments were performed internally in parallel to confirm that the Prolabel fragment alone was not stable in the cells and thus did not allow any activity to be measured.

1.3 Protocol 1.3.1 Experiment Plan
1) Inoculation of the cells on D0
2) Adherence for 24 hours under normoxia
3) Preparation and addition of the products (Biomek 2000 and FX) on D+1
4) Incubation under normoxia for 6 hours
5) Reading of the plates (by luminescence)

1.3.2 Inoculation of the Cells

The cells are inoculated with Multidrop in white, opaque-bottomed 384-well plates (Greiner ref 3704), in 30 µl of culture medium (1% FCS) a 10000 cells/well (cell plate).

1.3.3 Treatment

Preparation of the Dilution Plate (DL Plate)

The test products are prepared at $3\times10^{-2}$ M in 100% DMSO and then diluted to $3\times10^{-4}$ M in medium containing 0.1% FCS (10 µl in 990 µl of MEM). They are then deposited by hand into column 12 of a round-bottomed 96-well plate (200 µl of each compound) known as the dilution plate (dl). The complete DL plate of $3\times10^{-4}$ M to $10^{-9}$ M is then prepared with Biomek 2000 (programme: range of 10 points in series). For the references and controls, 100 µl of DMEM containing 0.1% FCS are added to column 1, 100 µl of Deferoxamine $10^{-3}$ M to column 2, wells A B C D and 100 µl of Deferoxamine $5\times10^{-3}$ M to column 2, wells E F G H.

DL Plate Distribution in Cell Plates 3.3 µL are taken from the DL plate by pipetting with a Biomek FX 96 and placed in horizontal duplicate (columns 1 to 24) in each 384-well cell plate (HEKEA_HIF1-alphaPLBL cell plate).

The cells are then placed for 6 hours in an incubator at 37° C. (ambient $O_2$, 6% $CO_2$).

1.3.4 Measurement of the Beta-Galactosidase Activity.

The kit used is the Prolabel chemiluminescent kit (Ref 93-0001 DiscoverX).

After incubation for 6 hours at 37° C., the cells are lysed with addition of 15 µl of lysis buffer containing the beta-galactosidase substrate (19 volumes of Path hunter cell assay buffer+5 volumes of Emarald II solution+1 volume of Galacton star) directly added to 30 µl of medium in the plate. The plates are incubated for 60 minutes in the absence of light, before reading the luminescence with a Top Count machine. The EC50 values for the compounds are then calculated with appropriate fitting software and given in Table III below.

The activating activity of a compound towards HIF is given by the molar concentration that produces 50% of the maximum response of this same compound.

TABLE III

| Compound No. | EC50 (M) |
| --- | --- |
| 1 | 8.8E−06 |
| 7 | 6.0E−06 |
| 9 | 1.4E−06 |

TABLE III-continued

| Compound No. | EC50 (M) |
|---|---|
| 13 | 5.2E−06 |
| 15 | 1.6E−05 |
| 16 | 8.6E−06 |
| 17 | 1.0E−05 |
| 18 | 4.4E−06 |
| 19 | 5.5E−06 |
| 20 | 3.4E−06 |
| 21 | 8.7E−06 |
| 23 | 1.2E−05 |
| 24 | 3.E−06 |
| 25 | 3.3E−06 |
| 26 | 1.5E−06 |
| 27 | 9.5E−06 |
| 28 | 1.6E−06 |
| 29 | 2.5E−06 |
| 30 | 6.5E−07 |
| 32 | 1.3E−06 |
| 33 | 9.4E−06 |
| 34 | 1.0E−05 |
| 35 | 2.5E−06 |
| 36 | 1.2E−06 |
| 37 | 2.2E−06 |
| 38 | 3.8E−06 |
| 60 | 2.1E−05 |
| 61 | 1.9E−06 |
| 62 | 3.9E−06 |

1.4 Various 1.4.1. Maintenance of the HEKEA_HIF1-Alpha PLBL Cells.

The cells are cultured in whole medium (cf. below) in a Flask T225. at 37° C. in a $CO_2$ incubator.

1.4.2. Culture Medium for the HEKEA_HIF1Alpha PLBL Cells

| DMEM | 500 mL |
|---|---|
| +FCS 10% (GIBCO 10500-056) | 50 mL |
| +Glutamine (2 mM final) | 5 mL |
| +Penicilllin + streptomycin (200 mg/mL) | 5 mL |
| +Hygromycin B (100 µg/mL) | 1.1 mL |
| +Geneticin (400 µg/mL final) | 4.4 mL |

2. Measurement of the Secretion of VEGF and EPO by Hep3B Hepatocytes 2.1. Object HIF is a transcription factor involved in the adaptation of cells to hypoxia. Since the genes activated by HIF are involved in the adaptive response of cells to hypoxia and of tissues to ischaemia, the object is to identify and characterize compounds that stabilize HIF1-alpha in cells in order to amplify or mimic its beneficial effect. HIF1-alpha was identified following the analysis of the EPO gene promoter, which makes this protein one of the first markers of HIF1-alpha activation. Moreover, VEGF is also identified in the literature as one of the main markers of HIF activation. It is for this reason that measurement of these two proteins was selected for characterizing compounds that are HIF activators in Hep3B cells.

The object was thus to develop a sensitive screening test, adaptable to 96-well plates, for directly measuring the amount of VEGF and EPO in the supernatant of the Hep3B cells (cells derived from a human hepatocarcinoma) in response to the potential HIF activators.

2.2. Test Principle

The test is an ELISA test for measuring VEGF and EPO in the supernatant of Hep3B cells treated under hypoxia or with deferoxamine as controls or with the potential HIF activators. The test was adapted to a 96-well plate, allowing greater compound screening capacity.

2.3. Protocol 2.3.1 Experiment Plan
1) Inoculation of the cells on D0
2) Adherence for 6 hours under normoxia
3) Preparation and addition of the products (Biomek 2000 and FX)
4) Incubation under normoxia for 18 hours
5) EPO and VEGF assay in the supernatant on D+1

2.3.2 Inoculation of the Cells

The cells are subcultured into 100 µl of culture medium (10% FCS) in black, opaque-bottomed 96-well plates (reference Costar 3916) at 30000 cells/well, with Multidrop.

2.3.3 Treatment of the Cells

Preparation of the Dilution Plate (DL Plate)

The test products are prepared at $10^{-2}$M in 100% DMSO and then diluted to $3×10^{-4}$M in medium containing 0.1% FCS (6 µl in 194 µl of MEM). 200 µl of each compound are deposited in column 12 of a 96-well plate. Dilution ranges from $3×10^{-4}$M to $3×10^{-8}$M are prepared with Biomek 2000 (programme: range of 9 points in series). 100 µl of MEM 0.1% FCS and Deferoxamine $5×10^{-3}$M are added as controls to column 3 and, respectively, to wells A,B,C,D & wells E,F,G,H DL Plate Distribution in Cell Plates The medium of the cells inoculated the day before into 96-well plates is changed for 90 µl of medium containing 0.1% FCS and 10 µl are distributed with FX 96 from the 96-well DL plates to the cell plates.

The cell plates thus treated are placed for 18 hours in an incubator at 37° C. (ambient $O_2$, 6% $CO_2$).

2.3.4 EPO and VEGF Assay

The supernatants (80 µl) of the Hep3B cells in the 96-well plates treated with the potential HIF activators are recovered with a multichannel pipette for simultaneous assay of the VEGF and the EPO by ELISA according to the supplier's instructions (Kit EPO Mesoscale (ref K15122B-2)). The EC50 values for EPO and VEGF of the compounds are then calculated with appropriate fitting software and reported in Table IV below.

2.4. Various

Culture Medium for the Hep3B Cells:

| MEM + Earles (GIBCO 310095) | 500 mL |
|---|---|
| +10% FCS (GIBCO 10500-056) | 50 mL |
| +Glutamine 2 mM final | 5 mL |
| +1% non-essential amino acids | 5 mL |

3. Results

The activating activity of a compound with respect to HIF is given by the concentration that produces 50% of the maximum response of this same compound in Table IV.

TABLE IV

| Compound No. | EC50 EPO (M) | EC50 VEGF (M) |
|---|---|---|
| 1 | 2.9E−06 | 3E−06 |
| 9 | 7.0E−07 | 6.6E−07 |
| 13 | 9.0E−07 | 1.0E−06 |
| 15 | 2.8E−06 | 3.0E−06 |
| 16 | 3.5E−06 | 3.0E−06 |
| 17 | 2.9E−06 | 2.9E−06 |

TABLE IV-continued

| Compound No. | EC50 EPO (M) | EC50 VEGF (M) |
|---|---|---|
| 18 | 5.0E−07 | 4.0E−07 |
| 19 | 2.4E−06 | 2.4E−06 |
| 20 | 1.0E−06 | 9.0E−07 |
| 21 | 1.4E−06 | 2.4E−06 |
| 24 | 5E−07 | 5E−07 |
| 25 | 2.4E−06 | 2.5E−06 |
| 26 | 1E−06 | 1.3E−06 |
| 28 | 1E−06 | 1E−06 |
| 29 | 2.5E−06 | 2.6E−06 |
| 30 | 1.5E−06 | 1.8E−06 |
| 32 | 2.6E−06 | 3.2E−06 |
| 35 | 1.7E−06 | 1.1E−06 |
| 36 | 1.6E−06 | 2E−06 |
| 59 | 2.6E−06 | 3.1E−06 |
| 61 | 2.2E−06 | 2.8E−06 |

The compounds according to the invention may thus be used for the preparation of medicaments, in particular medicaments that are activators of the HIF transcription factor.

Thus, according to another of its aspects, a subject of the invention is medicaments that comprise a compound of formula (I), or an addition salt thereof with a pharmaceutically acceptable acid of the compound of formula (I).

The invention also relates to a pharmaceutical composition comprising a compound of formula (I) according to the present invention, or a pharmaceutically acceptable salt of this compound, and also at least one pharmaceutically acceptable excipient.

These medicaments find their therapeutic use especially in treatment/prophylaxis, in particular of cardiovascular diseases, ischaemia of the lower limbs, cardiac insufficiency, coronary diseases of ischaemic origin, for instance angina pectoris or myocardial infarction, arteriosclerosis, strokes of ischaemic origin, pulmonary hypertension and any pathology caused by partial or total vascular occlusion in man and animals.

These medicaments also find their therapeutic use in the treatment/prophylaxis of glaucoma, renal diseases or in cerebral diseases of neurodegenerative origin or otherwise, and anaemia, or a medicament for promoting cicatrization or agents for shortening the post-operative convalescence period or a medicament for treating general fatigue conditions, or a medicament used for the purpose of obtaining blood in the context of autotransfusions necessary following major surgical interventions such as cranial or chest surgery, or cardiac, carotid or aortic operations.

These compounds find their therapeutic use especially in the treatment/prophylaxis of anaemia.

These compounds may also be used in man and animals for the purpose of obtaining blood in the context of autotransfusions necessary following major surgical interventions such as cranial or chest surgery or cardiac, carotid or aortic operations.

These compounds are potentially usable in man and animals as agents for promoting cicatrization or agents for shortening the post-operative convalescence period.

These compounds are potentially usable in man and animals in the treatment of general fatigue conditions ranging up to cachexia appearing in particular in the elderly.

These compounds are potentially usable in man and animals in the treatment of glaucoma, renal diseases or cerebral diseases of neurodegenerative origin or otherwise.

Finally, the compounds described in the invention are potentially usable in man and animals for treating cardiac or peripheral diseases of ischaemic origin via regenerative medicine in autologous and heterologous approaches using non-embryonic stem cells or myoblastic cells for therapeutic purposes, whether as treatment of these cells before administration or as treatment simultaneously with the local administration of these cells.

Moreover, the compounds described in the invention may be used, alone or, if necessary, in combination with one or more other active compounds that are useful in the treatment of hypertension, cardiac insufficiency, diabetes and anaemia.

For example, mention may be made of the combination of a compound according to the invention with one or more compounds chosen from converting enzyme inhibitors, angiotensin II receptor antagonists, beta-blockers, mineralocorticoid receptor antagonists, diuretics, calcium antagonists, statins and digitalin derivatives.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, nasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages do not depart from the scope of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration, to patient, of an effective dose of a compound according to the invention, or a pharmaceutically acceptable salt thereof.

We claim:
1. A compound of formula (I):

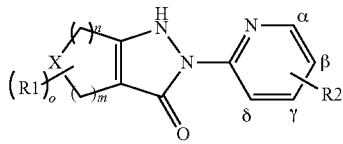

wherein:
n is equal to 0, 1 or 2;
m is equal to 0, 1 or 2, provided that m+n is 2;
o is equal to 0 or 1;
X represents a sulfur atom;
R1 represents oxo, —COOR5, —W—OH or —W—NR5R6, with W, R5 and R6 as defined below;
R2 represents hydrogen or a group chosen from (i) groups —(C1-C5)alkyl, (ii) groups —(C1-C5)alkoxy, (iii) groups —COOR5, (iv) groups —NR5R6, (v) groups —C(O)—NR5R6, (vi) groups —SO₂—NR3R4, (vii) heteroaryl groups optionally substituted with a group —(C1-C5)alkyl, (viii) groups —W-aryl, (ix) groups —W-heteroaryl, (x) groups —O—W-aryl, (xi) groups —O—W-heteroaryl and (xii) groups —O—W—NR5R6, with W, R3, R4, R5 and R6 as defined below;
R3 and R4,
(i) which may be identical or different, represent, independently of each other, hydrogen, —(C1-C5)alkyl, —(C3-C6)cycloalkyl, aryl, heteroaryl, —CH₂-heteroaryl, —(C1-C5)alkyl-NR5R6, —W—OH or —W—NR5R6; or
(ii) form, together with the nitrogen atom that bears them, a heterocycloalkyl group optionally substituted with one or more groups chosen from —(C1-C5)alkyl and —CH₂-aryl;
W is —(C1-C5)alkylene, optionally substituted with one or more hydroxyl groups; and
R5 and R6, which may be identical or different, represent, independently of each other, hydrogen, —(C1-C5)alkyl or —(C3-C6)cycloalkyl;
in the form of the base or of an acid-addition salt.

2. The compound according to claim 1, wherein:
R2 represents hydrogen, —(C1-C5)alkyl, —(C1-C5)alkoxy, —COOR5, —NR5R6, —C(O)—NR5R6 or —SO₂—NR3R4;
R3 and R4
(i) represent, independently of each other, hydrogen, —(C1-C5)alkyl, —(C3-C6)cycloalkyl, aryl, heteroaryl, —CH₂-heteroaryl or —(C1-C5)alkyl-NR5R6; or
(ii) form, together with the nitrogen atom that bears them, a heterocycloalkyl group optionally substituted with —(C1-C5)alkyl or aryl; and
R5 and R6 represent, independently of each other, hydrogen or —(C1-C5)alkyl;
in the form of the base or of an acid-addition salt.

3. The compound according to claim 1, wherein:
o is equal to 0;
R1 represents oxo, —CH₂-aryl, —C(O)R5- or —COOR5;
R3 and R4
(i) represent, independently of each other, hydrogen, —(C1-C5)alkyl, —(C3-C6)cycloalkyl, aryl, heteroaryl, —CH₂-heteroaryl or —(C1-C5)alkyl-NR5R6; or
(ii) form, together with the nitrogen atom that bears them, a heterocycloalkyl group optionally substituted with one or more group(s) —(C1-C5)alkyl or aryl, advantageously, the said heterocycloalkyl group representing a piperidyl group or a hexamethyleneimino group and the said aryl group representing a phenyl group;
R5 represents —(C1-C5)alkyl or —(C3-C6)cycloalkyl; and
R6 represents hydrogen or (C1-C5)alkyl;
in the form of the base or of an acid-addition salt.

4. The compound according to claim 3, wherein R1 represents benzyl; and R3 and R4 represent, independently of each other, phenyl, pyridyl or furyl, or R3 and R4 form, together with the nitrogen atom that bears them, piperidyl or hexamethyleneimino, wherein the piperidyl or hexamethyleneimino is optionally substituted with one or more —(C1-C5)alkyl or phenyl; in the form of the base or of an acid-addition salt.

5. The compound according to claim 1, wherein:
R1 represents oxo, COOR5, —W—OH or —W—NR5R6;
R2 represents —SO₂—NR3R4;
R3 and R4
(i) represent, independently of each other, hydrogen, —(C1-C5)alkyl, —(C3-C6)cycloalkyl, aryl, heteroaryl or —CH₂-heteroaryl, or
(ii) form, together with the nitrogen atom that bears them, a heterocycloalkyl group; and
R5 and R6 represent —(C1-C5)alkyl;
in the form of the base or of an acid-addition salt.

6. The compound according to claim 1, wherein:
R1 represents oxo;
R2 represents hydrogen, —(C1-C5)alkyl, —(C1-C5)alkoxy, —COOR5, —NR5R6 or —C(O)—NR5R6; and
R5 and R6 represent, independently of each other, hydrogen, —(C1-C5)alkyl or —(C3-C5)cycloalkyl;
in the form of the base or of an acid-addition salt.

7. The compound according to claim 1, wherein R2 represents hydrogen, —(C1-C5)alkyl, —(C1-C5)alkoxy, —COOR5, —NR5R6, —C(O)—NR5R6, heteroaryl substituted with —(C1-C5) alkyl, —O—W-aryl or —O—W-heteroaryl; in the form of the base or of an acid-addition salt.

8. The compound according to claim 1, wherein R2 represents —SO₂—NR3R4; in the form of the base or of an acid-addition salt.

9. The compound according to claim 1, wherein R2 is a substituent on the atom in the beta position of pyridine; in the form of the base or of an acid-addition salt.

10. The compound according to claim 1, wherein R2 is a substituent on the atom in the gamma position of pyridine; in the form of the base or of an acid-addition salt.

11. The compound according to claim 1, which is:
2-(4-methoxypyridin-2-yl)-1,2,4,6-tetrahydro-3H-thieno[3,4-c]pyrazol-3-one;
N-ethyl-6-(3-oxo-4,6-dihydro-1H-thieno[3,4-c]pyrazol-2(3H)-yl)-N-phenylpyridine-3-sulfonamide;
2-(pyridin-2-yl)-1,4,6,7-tetrahydrothiopyrano[4,3-c]pyrazol-3(2H)-one;
N-ethyl-6-(3-oxo-1,4,6,7-tetrahydrothiopyrano[4,3-c]pyrazol-2(3H)-yl)-N-phenylpyridine-3-sulfonamide;
N-ethyl-6-(3-oxo-3,5,6,7-tetrahydrothiopyrano[3,2-c]pyrazol-2(1H)-yl)-N-phenylpyridine-3-sulfonamide;
N,N-diethyl-6-(3-oxo-4,6-dihydro-1H-thieno[3,4-c]pyrazol-2(3H)-yl)pyridine-3-sulfonamide;
N,N-dimethyl-6-(3-oxo-4,6-dihydro-1H-thieno[3,4-c]pyrazol-2(3H)-yl)pyridine-3-sulfonamide;
2-[5-(pyrrolidin-1-ylsulfonyl)pyridin-2-yl]-1,2,4,6-tetrahydro-3H-thieno[3,4-c]-pyrazol-3-one;

N-cyclopropyl-6-(3-oxo-4,6-dihydro-1H-thieno[3,4-c]
  pyrazol-2(3H)-yl)pyridine-3-sulfonamide;
6-(3-oxo-4,6-dihydro-1H-thieno[3,4-c]pyrazol-2(3H)-
  yl)-N-(propan-2-yl)pyridine-3-sulfonamide;
N-tert-butyl-6-(3-oxo-4,6-dihydro-1H-thieno[3,4-c]pyra-
  zol-2(3H)-yl)pyridine-3-sulfonamide;
N-(furan-2-ylmethyl)-6-(3-oxo-4,6-dihydro-1H-thieno[3,
  4-c]pyrazol-2(3H)-yl)-pyridine-3-sulfonamide;
N-cyclopentyl-6-(3-oxo-4,6-dihydro-1H-thieno[3,4-c]
  pyrazol-2(3H)-yl)pyridine-3-sulfonamide;
N-methyl-6-(3-oxo-4,6-dihydro-1H-thieno[3,4-c]pyra-
  zol-2(3H)-yl)-N-(pyridin-2-yl)pyridine-3-sulfonamide;
2-(pyridin-2-yl)-1,2,4,6-tetrahydro-3H-thieno[3,4-c]
  pyrazol-3-one;
2-[4-(dimethylamino)pyridin-2-yl]-1,2,4,6-tetrahydro-
  3H-thieno[3,4-c]pyrazol-3-one;
2-{5-[(4-benzylpiperidin-1-yl)sulfonyl]pyridin-2-yl}-1,2,
  4,6-tetrahydro-3H-thieno[3,4-c]pyrazol-3-one;
6-(3-oxo-4,6-dihydro-1H-thieno[3,4-c]pyrazol-2(3H)-
  yl)-N-(pyridin-2-yl)pyridine-3-sulfonamide;
sodium 2-(4-ethylpyridin-2-yl)-2,6-dihydro-4H-thieno[3,
  4-c]pyrazol-3-olate;
2-[5-(azepan-1-ylsulfonyl)pyridin-2-yl]-1,2,4,6-tetrahy-
  dro-3H-thieno[3,4-c]pyrazol-3-one;
N-methyl-6-(3-oxo-4,6-dihydro-1H-thieno[3,4-c]pyra-
  zol-2(3H)-yl)-N-(pyridin-2-ylmethyl)pyridine-3-sul-
  fonamide;
tert-butyl 6-(3-oxo-4,6-dihydro-1H-thieno[3,4-c]pyrazol-
  2(3H)-yl)pyridine-3-carboxylate;
sodium 2-(4-methylpyridin-2-yl)-2,6-dihydro-4H-thieno
  [3,4-c]pyrazol-3-olate;
sodium 2-{5-[tert-butyl(methyl)sulfamoyl]pyridin-2-yl}-
  2,6-dihydro-4H-thieno[3,4-c]pyrazol-3-olate;
sodium 2-{5-[tert-butyl(ethyl)sulfamoyl]pyridin-2-yl}-2,
  6-dihydro-4H-thieno[3,4-c]pyrazol-3-olate;
sodium 2-(5-methylpyridin-2-yl)-2,6-dihydro-4H-thieno
  [3,4-c]pyrazol-3-olate;
sodium 2-[5-(tert-butylcarbamoyl)pyridin-2-yl]-2,6-dihy-
  dro-4H-thieno[3,4-c]pyrazol-3-olate;
sodium 2-(5-methoxypyridin-2-yl)-2,6-dihydro-4H-
  thieno[3,4-c]pyrazol-3-olate;
N-methyl-6-(3-oxo-4,6-dihydro-1H-thieno[3,4-c]pyra-
  zol-2(3H)-yl)-N-(pyridin-4-yl)pyridine-3-sulfonamide;
sodium 2-{5-[cyclopentyl(ethyl)sulfamoyl]pyridin-2-yl}-
  2,6-dihydro-4H-thieno[3,4-c]pyrazol-3-olate;
sodium 2-[4-(pyridin-3-ylmethoxy)pyridin-2-yl]-2,6-di-
  hydro-4H-thieno[3,4-c]pyrazol-3-olate;
cyclopentyl 6-(3-oxo-4,6-dihydro-1H-thieno[3,4-c]pyra-
  zol-2(3H)-yl)pyridine-3-carboxylate;
2-methylpropyl 6-(3-oxo-4,6-dihydro-1H-thieno[3,4-c]
  pyrazol-2(3H)-yl)pyridine-3-carboxylate;
2-[4-(propan-2-yl)pyridin-2-yl]-1,2,4,6-tetrahydro-3H-
  thieno[3,4-c]pyrazol-3-one;
sodium 2-[5-(propan-2-yl)pyridin-2-yl]-2,6-dihydro-4H-
  thieno[3,4-c]pyrazol-3-olate,
methyl 2-{5-[ethyl(phenyl)sulfamoyl]pyridin-2-yl}-3-
  oxo-2,3,4,6-tetrahydro-1H-thieno[3,4-c]pyrazole-4-
  carboxylate;
propan-2-yl 6-(3-oxo-4,6-dihydro-1H-thieno[3,4-c]pyra-
  zol-2(3H)-yl)pyridine-3-carboxylate;
sodium 2-[4-(pyridin-3-ylmethoxy)pyridin-2-yl]-2,6-di-
  hydro-4H-thieno[3,4-c]pyrazol-3-olate;
2,2-dimethylpropyl 6-(3-oxo-4,6-dihydro-1H-thieno[3,4-
  c]pyrazol-2(3H)-yl)pyridine-3-carboxylate;
2-[5-(5-tert-butyl-1,2,4-oxadiazol-3-yl)pyridin-2-yl]-1,2,
  4,6-tetrahydro-3H-thieno[3,4-c]pyrazol-3-one;
N-cyclopentyl-N-methyl-6-(3-oxo-4,6-dihydro-1H-
  thieno[3,4-c]pyrazol-2(3H)-yl)pyridine-3-sulfona-
  mide;
N-cyclopentyl-N-(2,3-dihydroxypropyl)-6-(3-oxo-4,6-di-
  hydro-1H-thieno[3,4-c]pyrazol-2(3H)-yl)pyridine-3-
  sulfonamide; or
2-[5-(3-tert-butyl-1,2,4-oxadiazol-5-yl)pyridin-2-yl]-1,2,
  4,6-tetrahydro-3H-thieno[3,4-c]pyrazol-3-one;
in the form of the base or of an acid-addition salt.

12. A process for preparing the compound according to claim 1, comprising reacting a compound of formula (IVa) or (IVb) or both:

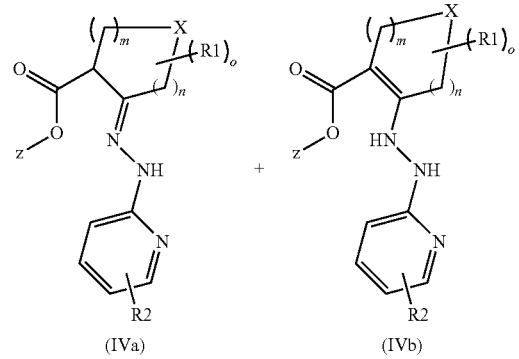

wherein X, R1, R2, n, m and are as defined in claim 1, and z represents an alkyl group, with an organic base.

13. A pharmaceutical composition, comprising the compound according to claim 1, or a pharmaceutically acceptable salt thereof, and at least one pharmaceutically acceptable excipient.

* * * * *